(12) United States Patent
Moberg et al.

(10) Patent No.: US 7,641,649 B2
(45) Date of Patent: Jan. 5, 2010

(54) RESERVOIR SUPPORT AND METHOD FOR INFUSION DEVICE

(75) Inventors: Sheldon B. Moberg, Thousand Oaks, CA (US); Ian B. Hanson, Northridge, CA (US); Paul S. Cheney, II, Winnetka, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 519 days.

(21) Appl. No.: 11/210,455

(22) Filed: Aug. 23, 2005

(65) Prior Publication Data
US 2006/0264888 A1 Nov. 23, 2006

Related U.S. Application Data

(60) Provisional application No. 60/678,290, filed on May 6, 2005.

(51) Int. Cl.
*A61K 9/22* (2006.01)
(52) U.S. Cl. .................................................. 604/890.1
(58) Field of Classification Search ............... 604/890.1, 604/131
See application file for complete search history.

(56) References Cited

U.S. PATENT DOCUMENTS

| | | | |
|---|---|---|---|
| 3,963,151 A | 6/1976 | North, Jr. | |
| 3,994,294 A | 11/1976 | Knute | |
| 4,089,624 A | 5/1978 | Nichols et al. | |
| 4,592,753 A * | 6/1986 | Panoz | 424/449 |
| 4,734,092 A * | 3/1988 | Millerd | 604/67 |
| 4,838,857 A | 6/1989 | Strowe et al. | |
| 4,886,499 A | 12/1989 | Cirelli et al. | |
| 4,976,696 A | 12/1990 | Sanderson et al. | |
| 5,002,527 A | 3/1991 | Reller et al. | |
| 5,053,001 A | 10/1991 | Reller et al. | |
| 5,062,834 A | 11/1991 | Gross et al. | |
| 5,090,963 A | 2/1992 | Gross et al. | |
| 5,156,591 A | 10/1992 | Gross et al. | |
| 5,176,502 A | 1/1993 | Sanderson et al. | |
| 5,186,805 A | 2/1993 | Gross et al. | |

(Continued)

FOREIGN PATENT DOCUMENTS

EP    1 347 705    12/2005

(Continued)

OTHER PUBLICATIONS

Copy of Notice of Allowance dated May 1, 2009 from related U.S. Appl. No. 11/210,467.

(Continued)

*Primary Examiner*—Nicholas D Lucchesi
*Assistant Examiner*—Aarti B Berdichevsky
(74) *Attorney, Agent, or Firm*—Foley & Lardner LLP

(57) ABSTRACT

An infusion media delivery device includes a durable housing portion and a separable disposable portion that selectively engage and disengage from each other. The disposable housing portion secures to the patient and may be disposed of after it has been in use for a prescribed period. The disposable housing portion supports an infusion media reservoir and a needle on a moveable platform. The platform is moveable between a first position in which a needle is disengaged with a patient and a second position in which the needle is engaged with the patient.

37 Claims, 17 Drawing Sheets

U.S. PATENT DOCUMENTS

| | | |
|---|---|---|
| 5,190,522 A | 3/1993 | Wojcicki et al. |
| 5,203,506 A | 4/1993 | Gross et al. |
| 5,205,819 A * | 4/1993 | Ross et al. .................. 604/67 |
| 5,232,449 A | 8/1993 | Stern et al. |
| 5,242,406 A | 9/1993 | Gross et al. |
| 5,242,408 A | 9/1993 | Jhuboo et al. |
| 5,246,147 A | 9/1993 | Gross et al. |
| 5,254,096 A | 10/1993 | Rondelet et al. |
| 5,259,732 A | 11/1993 | Stern |
| 5,259,835 A | 11/1993 | Clark et al. |
| 5,261,884 A | 11/1993 | Stern et al. |
| 5,295,966 A | 3/1994 | Stern et al. |
| 5,295,967 A | 3/1994 | Rondelet et al. |
| 5,312,364 A | 5/1994 | Jacobs |
| 5,356,632 A | 10/1994 | Gross et al. |
| 5,425,706 A | 6/1995 | Gross et al. |
| 5,527,288 A | 6/1996 | Gross et al. |
| 5,704,520 A | 1/1998 | Gross |
| 5,800,420 A | 9/1998 | Gross et al. |
| 5,807,375 A | 9/1998 | Gross et al. |
| 5,820,622 A | 10/1998 | Gross et al. |
| 5,848,991 A | 12/1998 | Gross et al. |
| 5,851,549 A | 12/1998 | Svec |
| 5,858,001 A | 1/1999 | Tsals et al. |
| 5,871,125 A | 2/1999 | Gross |
| 5,931,814 A | 8/1999 | Alex et al. |
| 5,951,523 A | 9/1999 | Osterlind et al. |
| 5,957,889 A | 9/1999 | Poulsen et al. |
| 5,984,894 A | 11/1999 | Poulsen et al. |
| 5,997,501 A | 12/1999 | Gross et al. |
| 6,003,736 A | 12/1999 | Ljunggren |
| 6,033,377 A | 3/2000 | Rasmussen et al. |
| 6,099,504 A | 8/2000 | Gross et al. |
| 6,186,982 B1 | 2/2001 | Gross et al. |
| 6,261,272 B1 | 7/2001 | Gross et al. |
| 6,275,717 B1 | 8/2001 | Gross et al. |
| 6,312,409 B1 | 11/2001 | Gross |
| 6,314,317 B1 | 11/2001 | Willis |
| 6,346,095 B1 | 2/2002 | Gross et al. |
| 6,346,099 B1 | 2/2002 | Altman |
| 6,364,865 B1 | 4/2002 | Lavi et al. |
| 6,406,455 B1 | 6/2002 | Willis et al. |
| 6,440,096 B1 | 8/2002 | Lastovich et al. |
| 6,474,219 B2 | 11/2002 | Klitmose et al. |
| 6,478,771 B1 | 11/2002 | Lavi et al. |
| 6,485,461 B1 | 11/2002 | Mason et al. |
| 6,490,483 B2 | 12/2002 | Willis |
| 6,508,788 B2 | 1/2003 | Preuthun |
| 6,537,251 B2 | 3/2003 | Klitmose |
| 6,585,707 B2 | 7/2003 | Cabiri et al. |
| 6,589,229 B1 | 7/2003 | Connelly et al. |
| 6,595,956 B1 | 7/2003 | Gross et al. |
| 6,607,513 B1 | 8/2003 | Down et al. |
| 6,613,019 B2 | 9/2003 | Munk |
| 6,616,627 B2 | 9/2003 | Willis et al. |
| 6,641,565 B1 | 11/2003 | Lavi et al. |
| 6,645,175 B2 * | 11/2003 | Kriesel et al. ................ 604/132 |
| 6,645,181 B1 | 11/2003 | Lavi et al. |
| 6,656,158 B2 | 12/2003 | Mahoney et al. |
| 6,656,159 B2 | 12/2003 | Flaherty |
| 6,669,669 B2 | 12/2003 | Flaherty et al. |
| 6,689,100 B2 | 2/2004 | Connelly et al. |
| 6,692,457 B2 | 2/2004 | Flaherty |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,723,068 B2 | 4/2004 | Lavi et al. |
| 6,723,072 B2 | 4/2004 | Flaherty et al. |
| 6,740,059 B2 | 5/2004 | Flaherty |
| 6,749,587 B2 | 6/2004 | Flaherty |
| 6,749,589 B1 | 6/2004 | Douglas et al. |
| 6,767,188 B2 | 7/2004 | Vrane et al. |
| 6,768,425 B2 | 7/2004 | Flaherty et al. |
| 6,786,246 B2 | 9/2004 | Ohms et al. |
| 6,808,506 B2 | 10/2004 | Lastovich et al. |
| 6,809,653 B1 | 10/2004 | Mann et al. |
| 6,830,558 B2 | 12/2004 | Flaherty et al. |
| 6,830,560 B1 | 12/2004 | Gross et al. |
| 6,899,699 B2 | 5/2005 | Enggaard |
| 6,918,894 B2 | 7/2005 | Fleury et al. |
| 6,936,006 B2 | 8/2005 | Sabra |
| 6,939,324 B2 | 9/2005 | Gonnelli et al. |
| 6,948,918 B2 | 9/2005 | Hansen |
| 6,952,604 B2 | 10/2005 | DeNuzzio et al. |
| 6,960,184 B2 | 11/2005 | Willis et al. |
| 6,960,192 B1 | 11/2005 | Flaherty et al. |
| 6,984,218 B2 * | 1/2006 | Nayak et al. ................ 604/6.11 |
| 6,991,620 B2 | 1/2006 | Marano-Ford et al. |
| 6,997,911 B2 | 2/2006 | Klitmose |
| 7,004,928 B2 | 2/2006 | Aceti et al. |
| 7,008,399 B2 | 3/2006 | Larsen et al. |
| 7,018,360 B2 | 3/2006 | Flaherty et al. |
| 7,027,478 B2 | 4/2006 | Ackley |
| 7,029,455 B2 | 4/2006 | Flaherty |
| 7,083,592 B2 | 8/2006 | Lastovich et al. |
| 7,083,599 B2 | 8/2006 | Alchas et al. |
| 7,115,108 B2 | 10/2006 | Wilkinson et al. |
| 7,128,727 B2 | 10/2006 | Flaherty et al. |
| 7,133,329 B2 | 11/2006 | Skyggebjerg et al. |
| 7,137,964 B2 | 11/2006 | Flaherty |
| 7,144,384 B2 | 12/2006 | Gorman et al. |
| 7,150,409 B2 | 12/2006 | Gonnelli et al. |
| 7,156,838 B2 | 1/2007 | Gabel et al. |
| 7,187,969 B2 | 3/2007 | Willis |
| 7,250,037 B2 * | 7/2007 | Shermer et al. ............ 604/134 |
| 7,297,151 B2 | 11/2007 | Boecker et al. |
| 7,544,185 B2 | 6/2009 | Bengtsson |
| 2002/0040208 A1 | 4/2002 | Flaherty et al. |
| 2002/0072733 A1 | 6/2002 | Flaherty |
| 2002/0107492 A1 * | 8/2002 | Brach et al. ................. 604/296 |
| 2002/0123740 A1 | 9/2002 | Flaherty et al. |
| 2002/0126036 A1 | 9/2002 | Flaherty et al. |
| 2002/0169439 A1 | 11/2002 | Flaherty |
| 2002/0173748 A1 * | 11/2002 | McConnell et al. .... 604/167.02 |
| 2003/0055380 A1 | 3/2003 | Flaherty |
| 2003/0073952 A1 | 4/2003 | Flaherty et al. |
| 2003/0097092 A1 | 5/2003 | Flaherty |
| 2003/0167035 A1 | 9/2003 | Flaherty et al. |
| 2003/0167036 A1 | 9/2003 | Flaherty |
| 2003/0195491 A1 * | 10/2003 | Schneider et al. ........ 604/890.1 |
| 2003/0199824 A1 | 10/2003 | Mahoney et al. |
| 2003/0199825 A1 | 10/2003 | Flaherty |
| 2003/0229310 A1 | 12/2003 | Flaherty et al. |
| 2004/0010207 A1 | 1/2004 | Flaherty et al. |
| 2004/0015131 A1 | 1/2004 | Flaherty et al. |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0116866 A1 | 6/2004 | Gorman et al. |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0022274 A1 | 1/2005 | Campbell et al. |
| 2006/0264835 A1 | 11/2006 | Nielsen et al. |
| 2006/0282290 A1 * | 12/2006 | Flaherty et al. ................ 705/2 |
| 2007/0071596 A1 | 3/2007 | Ryser et al. |
| 2008/0051709 A1 * | 2/2008 | Mounce et al. ............ 604/131 |
| 2008/0051765 A1 * | 2/2008 | Mounce ................ 604/890.1 |
| 2008/0077081 A1 * | 3/2008 | Mounce et al. ............... 604/67 |

| | | | |
|---|---|---|---|
| 2008/0255516 A1 * | 10/2008 | Yodfat et al. | 604/151 |

FOREIGN PATENT DOCUMENTS

| | | |
|---|---|---|
| EP | 1 423 079 | 7/2006 |
| EP | 1 135 056 | 8/2006 |
| EP | 1 702 635 | 9/2006 |
| EP | 1 545 657 | 11/2006 |
| EP | 1 546 556 | 12/2006 |
| EP | 1 341 569 | 1/2007 |
| EP | 1 461 070 | 1/2007 |
| EP | 1 464 351 | 1/2007 |
| EP | 1 309 366 | 2/2007 |
| EP | 0 944 648 | 3/2007 |
| EP | 1 646 412 | 3/2007 |
| EP | 1 095 668 | 4/2007 |
| WO | WO 01/76684 A1 | 10/2001 |
| WO | WO 02/20073 A2 | 3/2002 |
| WO | WO 02/28454 A2 | 4/2002 |
| WO | WO 02/40083 A2 | 5/2002 |
| WO | WO 02/49509 A2 | 6/2002 |
| WO | WO 02/068015 A2 | 9/2002 |
| WO | WO 03/024504 A2 | 3/2003 |
| WO | WO 03/033051 A1 | 4/2003 |
| WO | WO 03/059372 A2 | 7/2003 |
| WO | WO 03/059372 A3 | 7/2003 |
| WO | WO 03/074121 A1 | 9/2003 |
| WO | WO 03/090509 A2 | 11/2003 |
| WO | WO 03/090819 A2 | 11/2003 |
| WO | WO 03/090838 A1 | 11/2003 |
| WO | WO 03/103758 A1 | 12/2003 |
| WO | WO 03/103763 A1 | 12/2003 |
| WO | WO 2004/006981 A2 | 1/2004 |
| WO | WO 2004/006982 A2 | 1/2004 |
| WO | WO 2004/030716 A2 | 4/2004 |
| WO | WO 2004/030717 A2 | 4/2004 |
| WO | WO 2004/060436 A2 | 7/2004 |
| WO | WO 2004/093648 A2 | 11/2004 |
| WO | WO 2004/098390 A2 | 11/2004 |
| WO | WO 2004/098454 A2 | 11/2004 |
| WO | WO 2006/015922 A1 | 2/2006 |
| WO | WO 2006/018425 A2 | 2/2006 |
| WO | WO 2006/018425 A3 | 2/2006 |
| WO | WO 2006/018447 A2 | 2/2006 |
| WO | WO 2006/018447 A3 | 2/2006 |
| WO | WO 2006/024671 A1 | 3/2006 |
| WO | WO 2006/024672 A1 | 3/2006 |
| WO | WO 2006/042811 A2 | 4/2006 |
| WO | WO 2006/042811 A3 | 4/2006 |
| WO | WO 2006/072416 A2 | 7/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/084464 A1 | 8/2006 |
| WO | WO 2006/086980 A1 | 8/2006 |
| WO | WO 2006/089547 A1 | 8/2006 |
| WO | WO 2006/089548 A1 | 8/2006 |
| WO | WO 2006/089965 A1 | 8/2006 |
| WO | WO 2006/096746 A1 | 9/2006 |
| WO | WO 2006/097453 A1 | 9/2006 |
| WO | WO 2006/104806 A2 | 10/2006 |
| WO | WO 2006/108775 A2 | 10/2006 |
| WO | WO 2006/108809 A1 | 10/2006 |
| WO | WO 2006/116997 A1 | 11/2006 |
| WO | WO 2006/120253 A2 | 11/2006 |
| WO | WO 2006/125692 A1 | 11/2006 |
| WO | WO 2007/000425 A2 | 1/2007 |
| WO | WO 2007/000426 A2 | 1/2007 |
| WO | WO 2007/000427 A1 | 1/2007 |

OTHER PUBLICATIONS

Copy of Office Action dated May 30, 2008 from related U.S. Appl. No. 11/211,150.
Copy of Office Action dated Dec. 12, 2008 from related U.S. Appl. No. 11/211,150.
Copy of Office Action dated Mar. 18, 2009 from related U.S. Appl. No. 11/211,095.
Copy of Office Action dated Jul. 20, 2009 from related U.S. Appl. No. 11/211,157.
Copy of Office Action dated Sep. 18, 2009 from related U.S. Appl. No. 11/211,143.

* cited by examiner

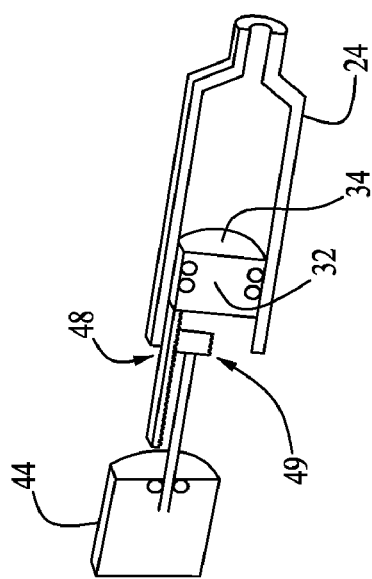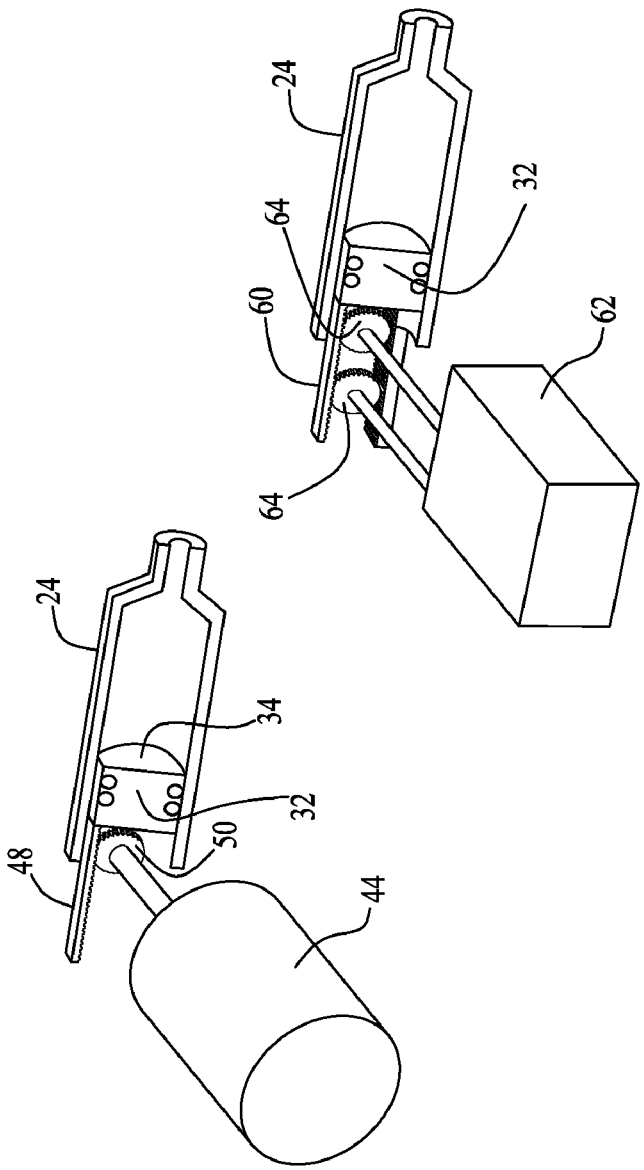
FIG. 4
FIG. 5
FIG. 6

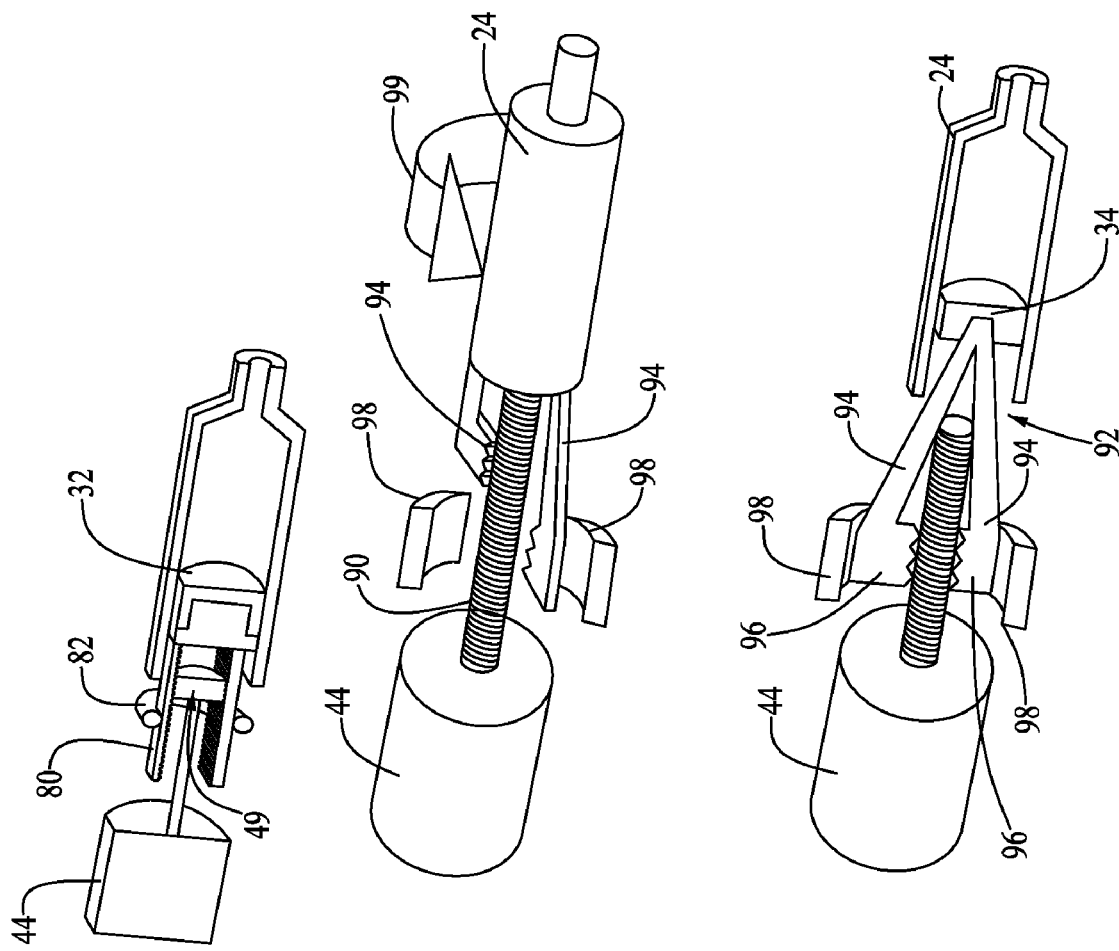

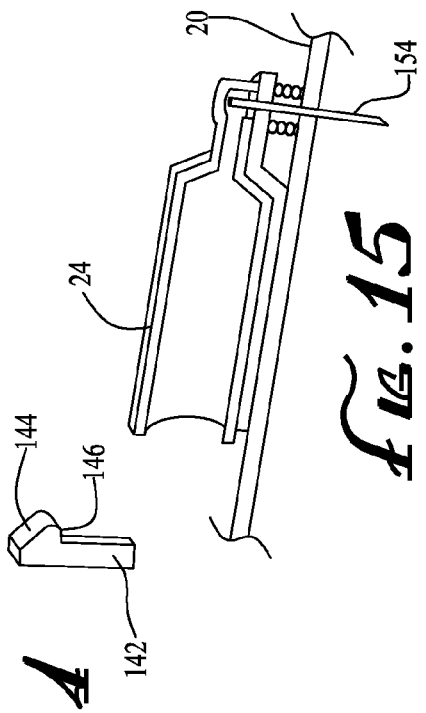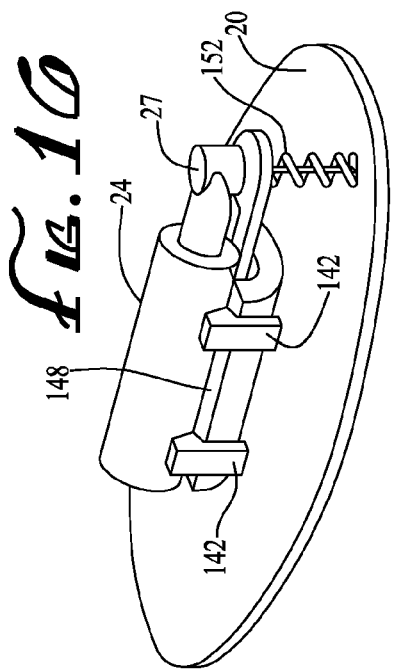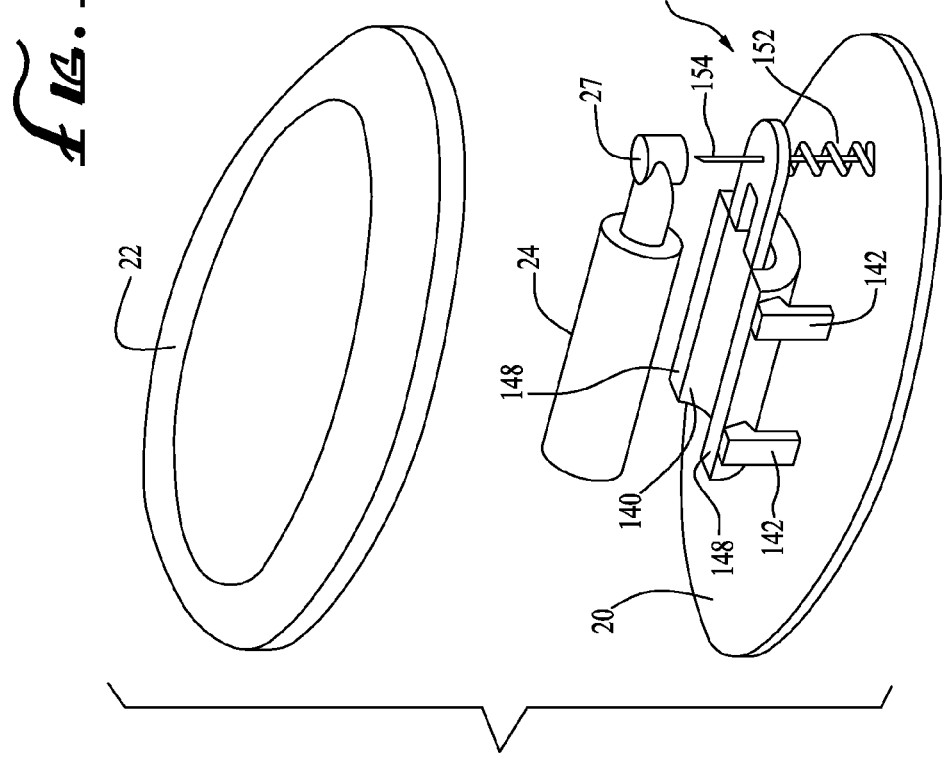

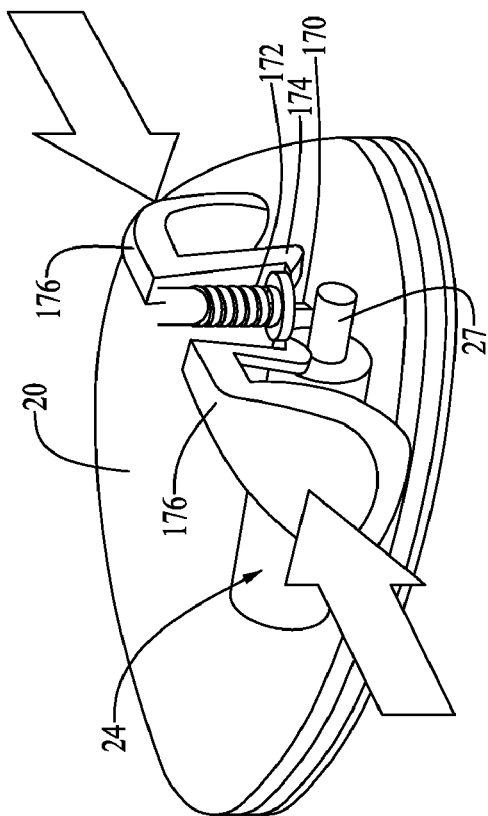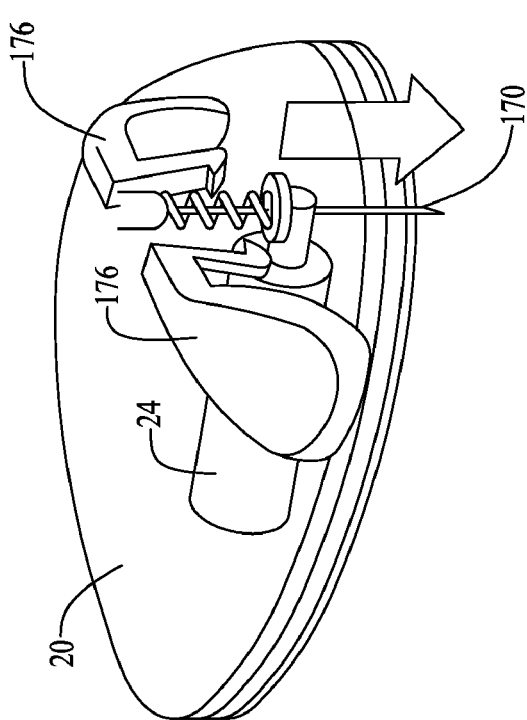

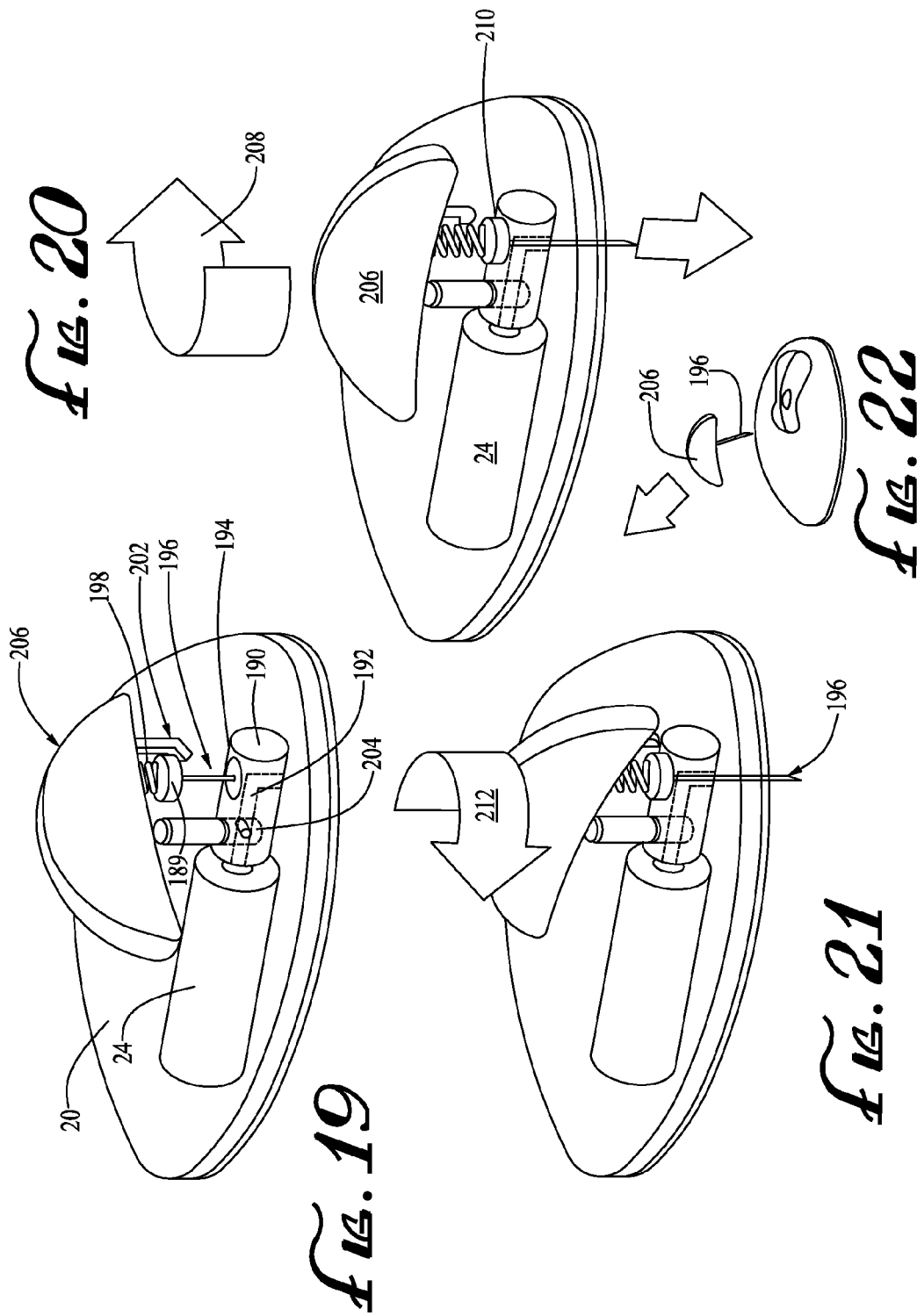

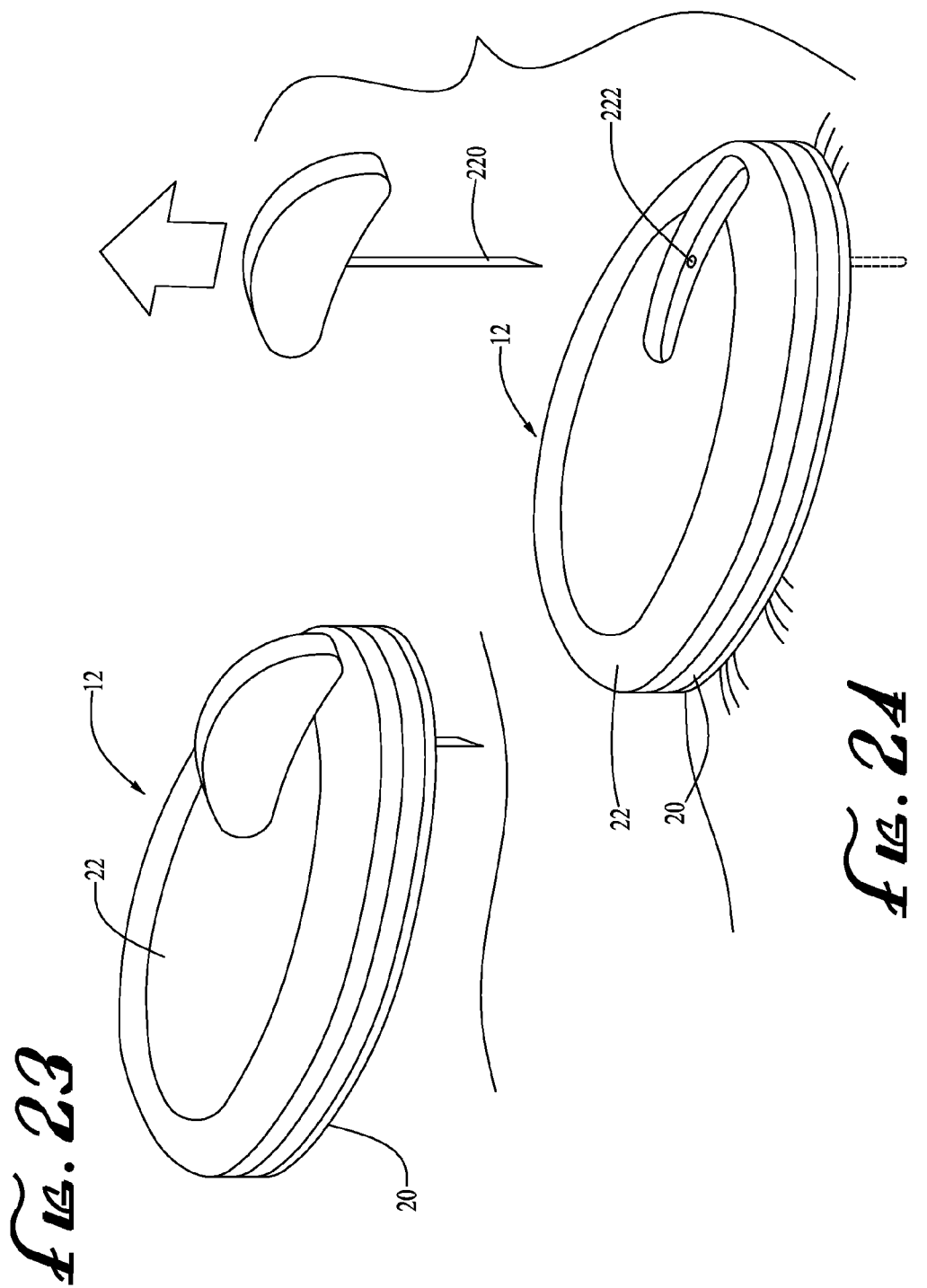

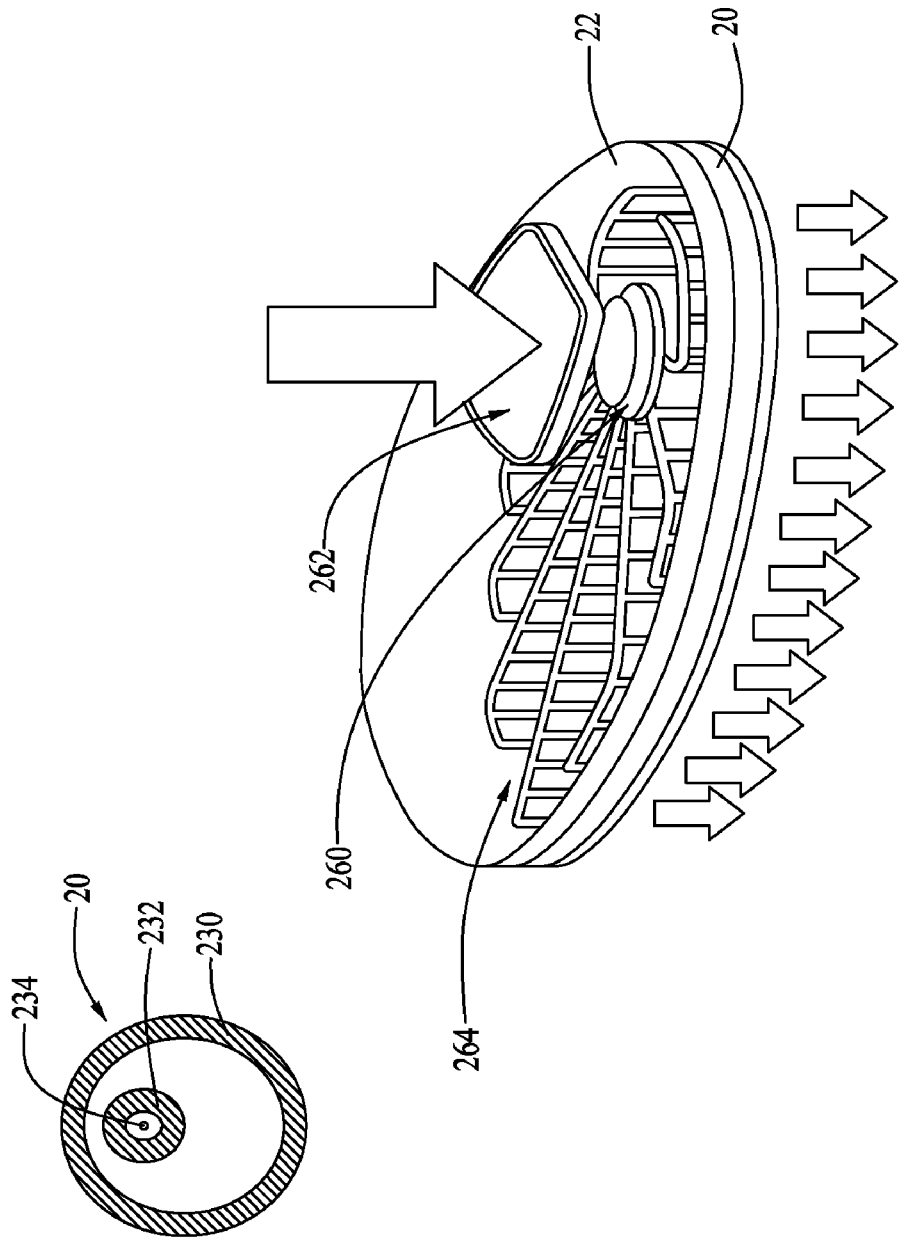

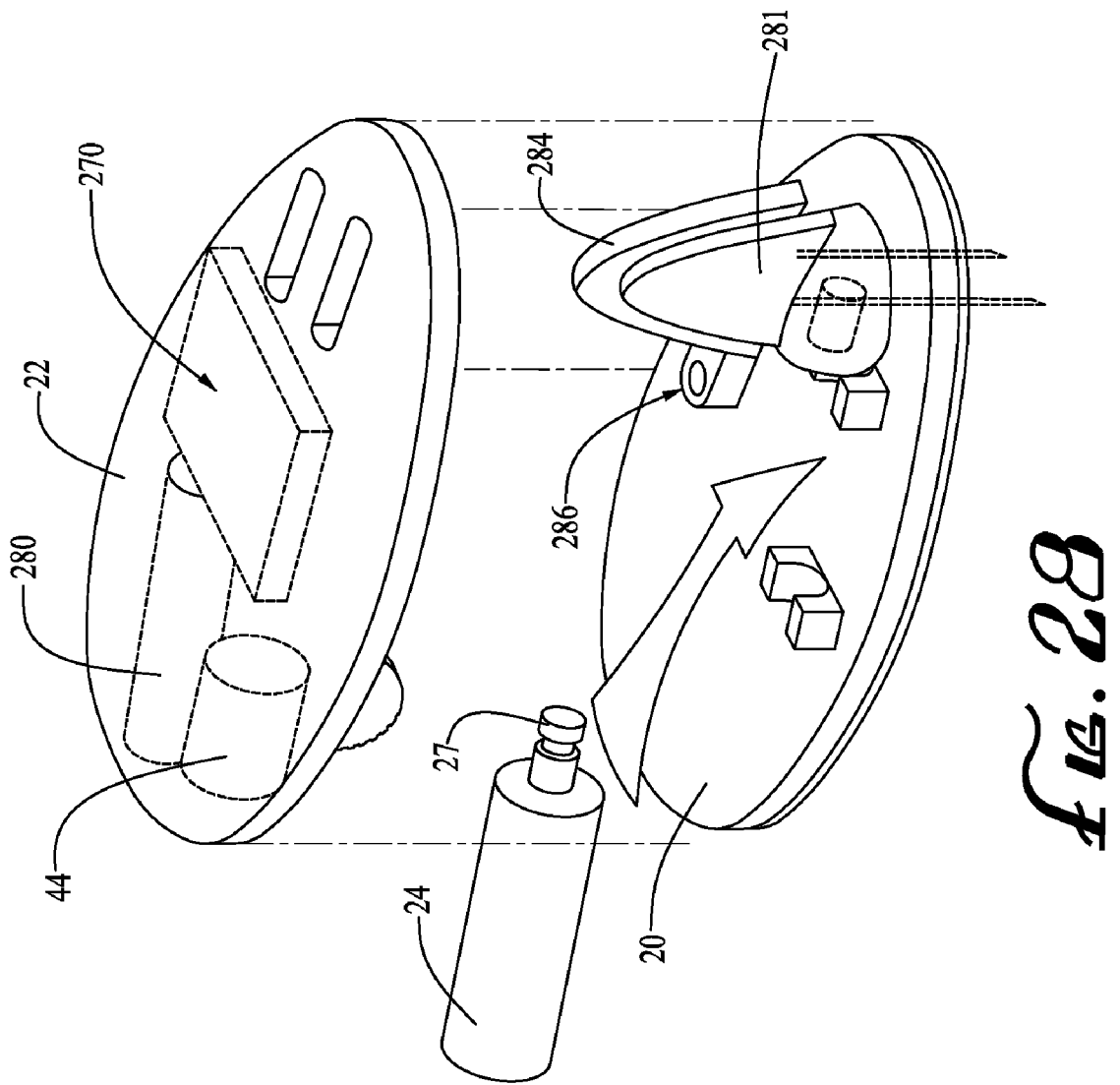

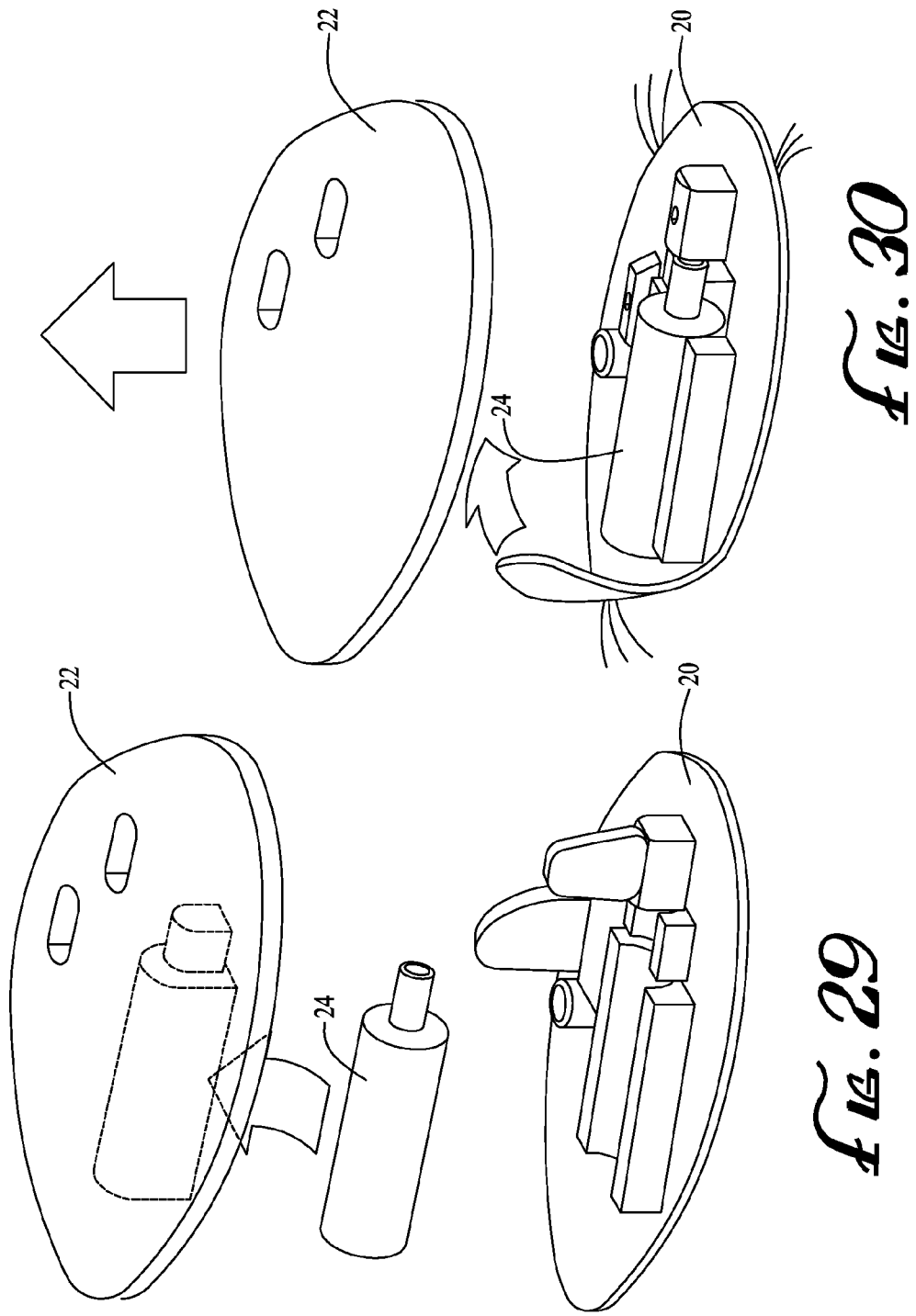

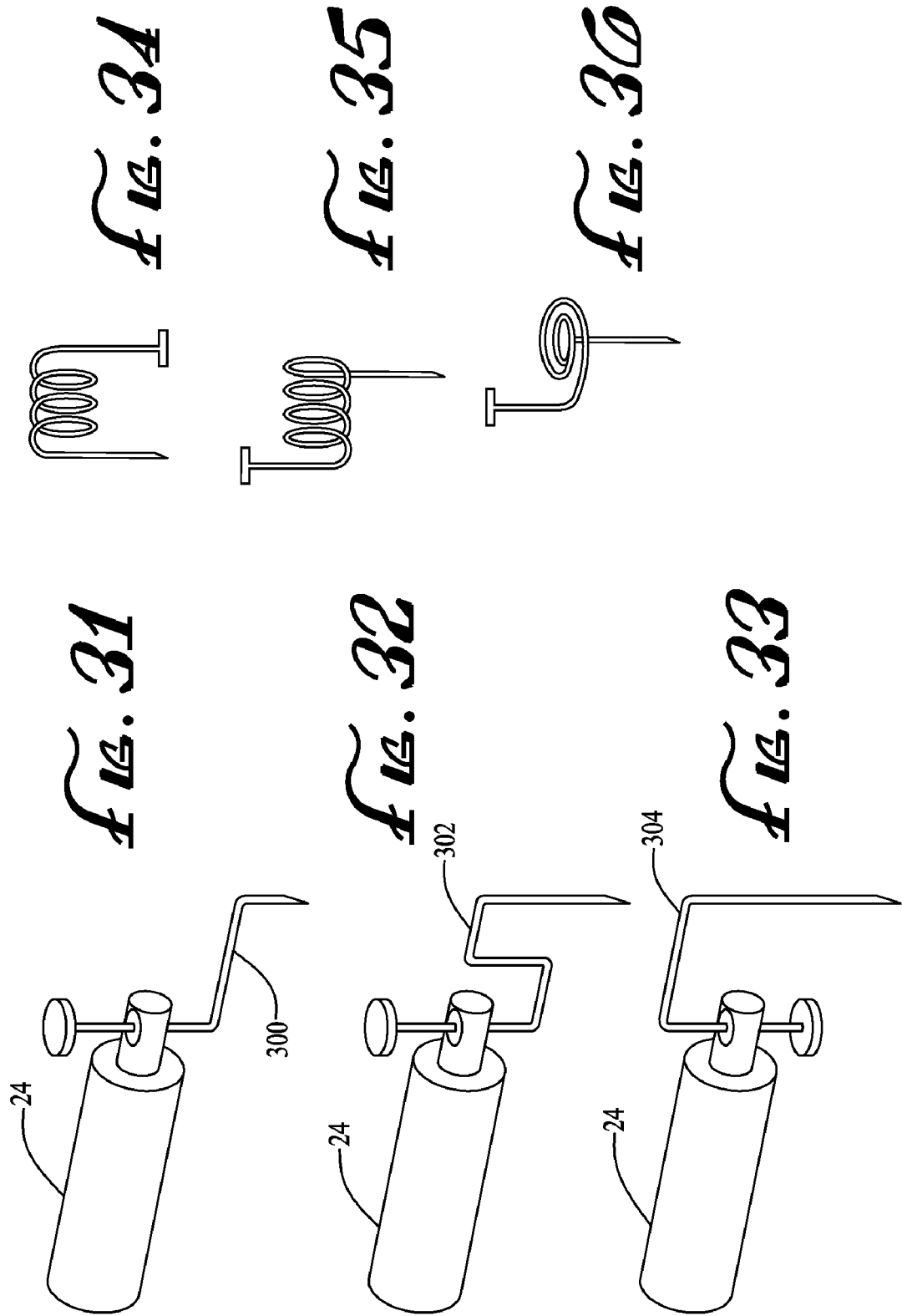

RESERVOIR SUPPORT AND METHOD FOR INFUSION DEVICE

CROSS-REFERENCE TO RELATED PATENT APPLICATIONS

The present invention relates to U.S. Application 60/678,290, filed May 6, 2005, which is incorporated herein by reference in its entirety and from which the priority benefit under 35 USC 119(e) is claimed.

BACKGROUND OF THE INVENTION

Certain chronic diseases may be treated, according to modern medical techniques, by delivering a medication or other substance to a patient's body, either in a continuous manner or at particular times or time intervals within an overall time period. For example, diabetes is a chronic disease that is commonly treated by delivering defined amounts of insulin to the patient at appropriate times. Some common modes of providing an insulin therapy to a patient include delivery of insulin through manually operated syringes and insulin pens. However, other modern systems employ programmable pumps to deliver controlled amounts of insulin to a patient.

Pump type delivery devices have been configured in external devices (that connect to a patient) or implantable devices (to be implanted inside of a patient's body). External pump type delivery devices include devices designed for use in a stationary location (for example, in a hospital or clinic), and further devices configured for ambulatory or portable use (to be carried by a patient). Examples of some external pump type delivery devices are described in Published PCT Application WO 01/70307 (PCT/US01/09139) titled "Exchangeable Electronic Cards For Infusion Devices" (which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advision Patients Concerning Doses Of Insulin," and U.S. Pat. No. 6,589,229 titled "Wearable Self-Contained Drug Infusion Device," each of which is incorporated herein by reference in its entirety.

External pump type delivery devices may be connected in fluid-flow communication to a patient-user, for example, through a suitable hollow tubing. The hollow tubing may be connected to a hollow needle that is designed to pierce the patient-user's skin and deliver infusion media there-through. Alternatively, the hollow tubing may be connected directly to the patient as or through a cannula.

In contexts in which the hollow tubing is connected to the patient through a hollow needle that pierces the patient's skin, a manual insertion of the needle into the patient can be somewhat traumatic to the patient. Accordingly, insertion tools have been made to assist the insertion of a needle into the patient, whereby a needle is forced by a spring to quickly move from a retracted position into an extended position. One example of such an insertion tool is described in U.S. Patent Application Publication No. 2002/0022855, titled "Insertion Device For An Insertion Set And Method Of Using The Same" (assigned to the assignee of the present invention), which is incorporated herein by reference in its entirety. As the needle is moved into the extended position, the needle is quickly forced through the patient's skin in a single, relatively abrupt motion that can be less traumatic to a patient as compared to a slower, manual insertion of a needle.

As compared to syringes and insulin pens, pump type delivery devices can be significantly more convenient to a patient, in that accurate doses of insulin may be calculated and delivered automatically to a patient at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump type delivery devices have become an important aspect of modern medical treatments of various types of medical conditions, such as diabetes. As pump technologies improve and doctors and patients become more familiar with such devices, the popularity of external medical infusion pump treatment increases and is expected to increase substantially over the next decade.

However, many types of pump type delivery devices have been relatively expensive to obtain and to operate over a period of time. Some pump type delivery devices require relatively complicated and time consuming procedures for re-filling or replacing spent infusion media. Some pump type delivery devices can only be used for a prescribed period of time or require disposal or substantial rebuilding of key components after a prescribed number of uses.

Accordingly, a need exists for an infusion pump device and system that meets the increased demand for ambulatory infusion devices and that combines beneficial features of prior pump devices (including capabilities for continuous infusion, precision dosing, programmable delivery schedules, controlled operation based on sensor or monitor data) with additional features that allow the pump device and system to be operated economically and efficiently over a sufficient length of time. A further need exists for such infusion pump devices and systems which include features for simplifying re-filling or replacement of infusion media.

BRIEF DESCRIPTION OF THE DRAWINGS

FIGS. 3-12 each show a partial cross-sectional view of elements of a delivery device, including a motor, linkage and reservoir for a delivery device according to an embodiment of the present invention.

FIGS. 13 is a partially exploded view of a delivery device according to an embodiment of the invention.

FIGS. 14-16 show perspective views of various elements of the delivery device of FIG. 13.

FIGS. 17-24 and 28-30 each show a generalized perspective view of needle insertion portions of delivery devices according to embodiments of the present invention.

FIG. 25 is a bottom view of a disposable portion of a delivery device according to an embodiment of the present invention.

FIG. 26 is a perspective view of a delivery device, showing internal structure for distributing adhesive release agents according to an embodiment of the present invention.

FIGS. 31-36 are generalized perspective views of various needle configurations according to embodiments of the present invention.

DETAILED DESCRIPTION

The present invention relates, generally, to delivery devices, systems and methods for delivering infusion media, such as a drug, to a recipient, such as a medical patient. In particular embodiments, a delivery device includes a disposable portion that secures to the recipient and that may be readily disposed of after it has been in use for a period of time. Such embodiments may be configured to provide a reliable, user-friendly mechanism to secure the delivery device to a patient for delivery of fluidic infusion media to the patient. Embodiments may be configured with feature that enhance the ease by which patients may secure the delivery device to the patient's skin and further features that enhance the ease by which patients may fill, re-fill or replace spent infusion media.

While embodiments of the present invention are described herein with reference to an insulin delivery example for treating diabetes, other embodiments of the invention may be employed for delivering other infusion media to a patient for other purposes. For example, further embodiments of the invention may be employed for delivering other types of drugs to treat diseases or medical conditions other than diabetes, including, but not limited to drugs for treating pain or certain types of cancers, pulmonary disorders or HIV. Further embodiments may be employed for delivering media other than drugs, including, but not limited to, nutritional media including nutritional supplements, dyes or other tracing media, saline or other hydration media, or the like.

Figure 1:
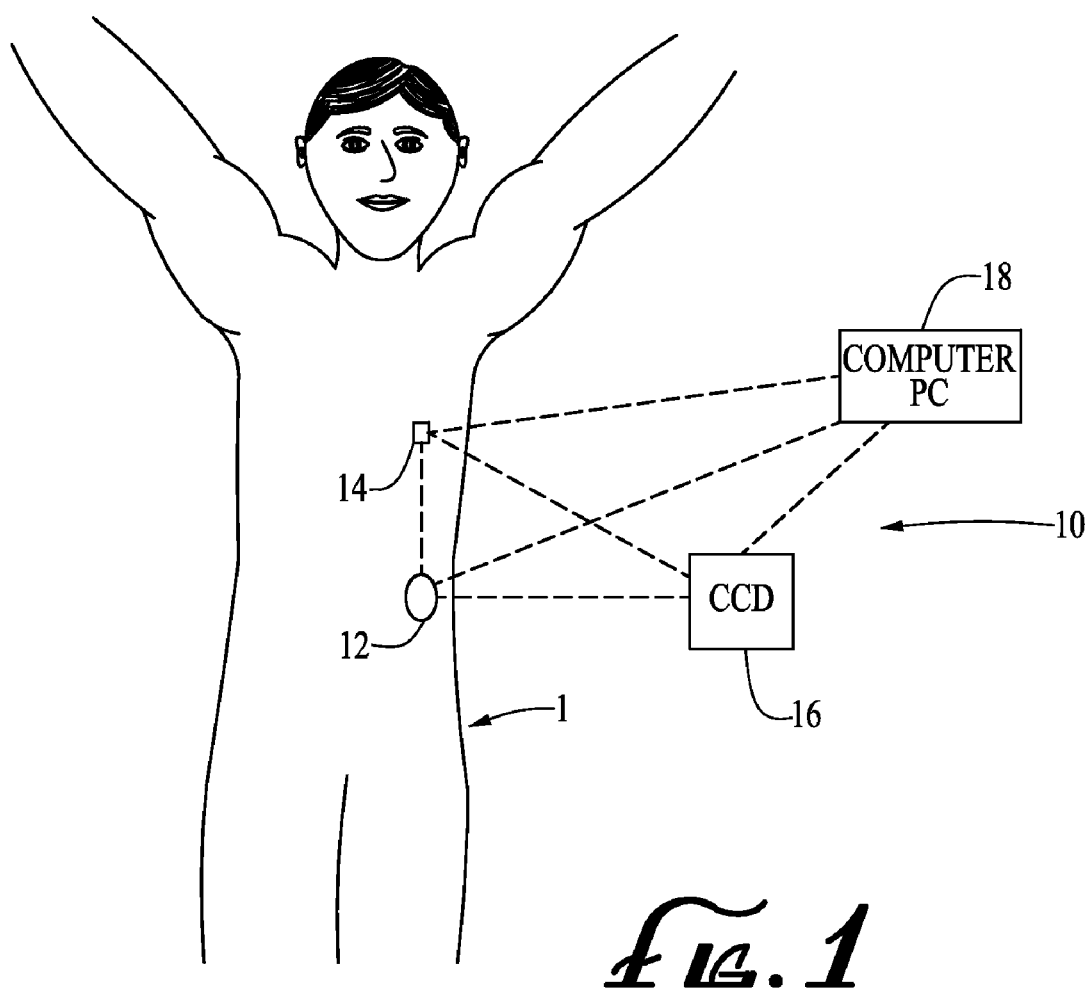
FIG. 1 is a generalized diagram of a delivery system in relation to a human patient-user.

A generalized representation of an infusion media delivery system 10 is shown in FIG. 1, wherein the system includes a delivery device 12 configured according to embodiments of the invention described herein. The system 10 may also include other components coupled for communication with the delivery device 12, including, but not limited to, a sensor or monitor 14, a command control device (CCD) 16 and a computer 18. Each of the CCD 16, the computer 18 and the delivery device 12 may include receiver or transceiver electronics that allow communication with other components of the system. The delivery device 12 may include electronics and software for analyzing sensor data and for delivering infusion media according to sensed data and/or pre-programmed delivery routines. Some of the processing, delivery routine storage and control functions may be carried out by the CCD 16 and/or the computer 18, to allow the delivery device 12 to be made with more simplified electronics. However, in other embodiments, the system 10 may comprise delivery device 12 without any one or more of the other components of the system 10 shown in FIG. 1.

In the generalized system diagram of FIG. 1, the delivery device 12 and sensor or monitor 14 are secured to a patient-user. The locations at which those components are secured to the patient-user in FIG. 1 are provided only as a representative, non-limiting example. The delivery device 12 and sensor or monitor 14 may be secured at other locations on the patient, and such locations may depend upon the type of treatment to be administered by the system 10.

As described in further detail below, the delivery device 12 contains a reservoir of infusion media and delivers the infusion media into the patient's body in a controlled manner. The delivery device 12 may be configured to secure to the skin of a patient, in the manner of a patch, at a desired location on the patient. Control instructions and/or data may be communicated between the delivery device 12, the sensor or monitor 14, the CCD 16 and the computer 18, as described in more detail below.

Figure 2:
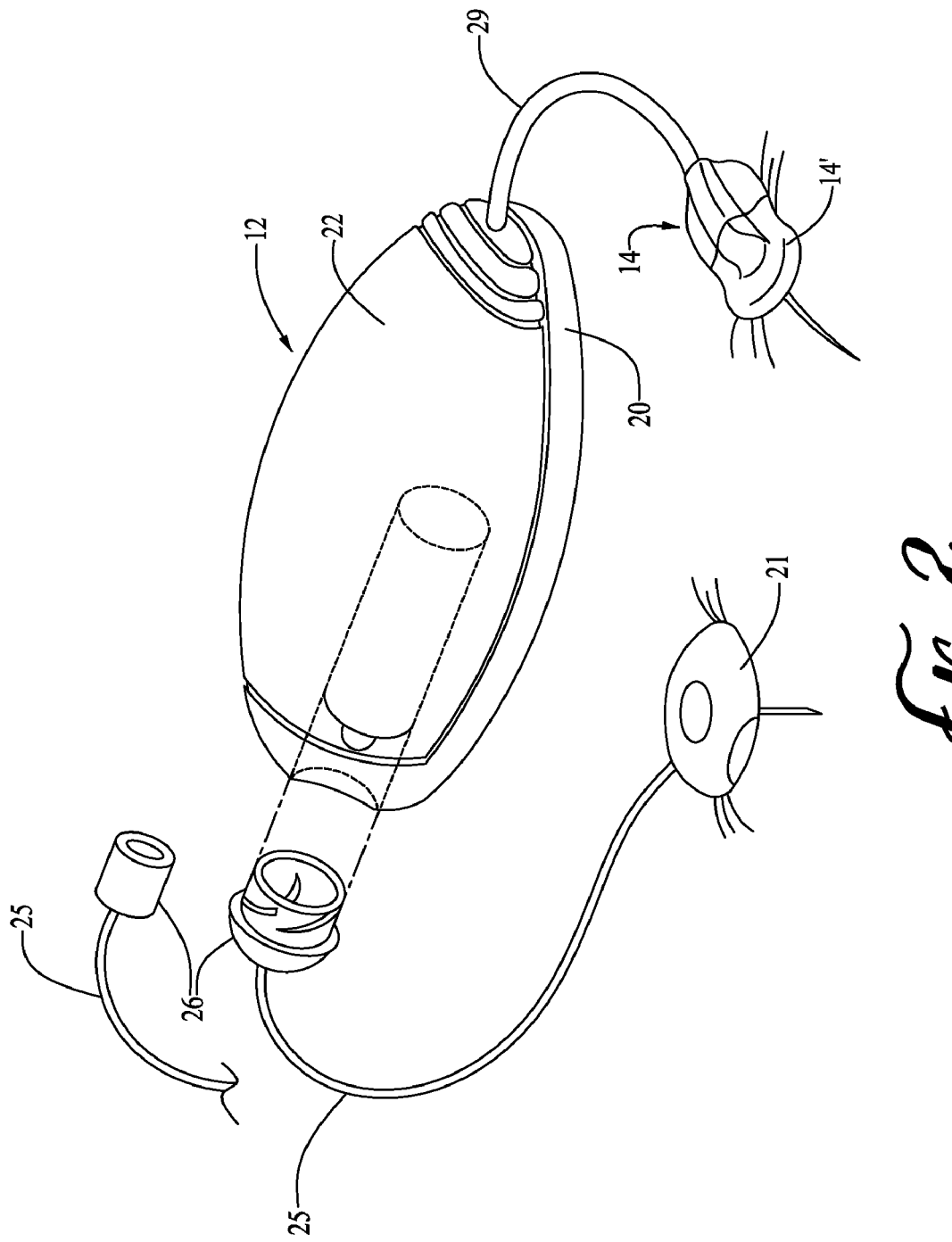
FIG. 2 is a perspective view of a delivery device and related components according to an embodiment of the invention.

An example of a patch-like delivery device 12 according to an embodiment of the invention is shown in FIG. 2. The delivery device 12 in FIG. 2 includes a disposable portion 20 and a durable portion 22. The disposable portion 20 may include structural elements that ordinarily contact the patient's skin or infusion media, during operation of the delivery device 12. On the other hand, the durable portion 22 may have elements (including electronics, motor components, linkage components, and the like) that do not ordinarily contact the patient or infusion media during operation of the delivery device 12. Thus, elements in the durable portion 22 of the delivery device 12 are typically not contaminated from contact with the patient or infusion media during normal operation of the delivery device 12.

In the illustrated embodiment, the disposable portion of the delivery device 12 comprises a disposable base 20 that supports a reservoir 24. The durable portion 22 may comprise a housing that secures onto the base 20 and covers the reservoir 24. The durable portion 22 may house a suitable drive device, such as an electrically operated motor (not shown in FIG. 2), and drive linkage components (not shown in FIG. 2) for driving fluid out of the reservoir. The durable portion 22 also may house suitable control electronics (not shown in FIG. 2) for controlling the operation of the drive device to drive fluid from the reservoir in a controlled manner. Further embodiments may include communication electronics (not shown in FIG. 2) within the durable portion 22, for communicating with the sensor or monitor 14, the CCD 16, the computer 18 and/or other components of the system 10.

The disposable base portion 20 has a bottom surface (facing downward and into the page in FIG. 2) that is configured to secure to a patient's skin at a desired location on the patient. A suitable adhesive may be employed at the interface between the bottom surface of the base portion 20 and the patient's skin, to adhere the base portion 22 to the patient's skin. The adhesive may be provided on the bottom surface of the base portion 20, with a pealable cover layer covering the adhesive material. In this manner, a patient-user may peal off the cover layer to expose the adhesive material and then place the adhesive side of the base portion 20 against the patient's skin.

The base portion 20 may include a suitable opening or port 23 for connecting a hollow tube 25 to the reservoir, to convey infusion media from the reservoir. One end of the tube 25 may have a suitable connector 26, such as, but not limited to a Luer connector or a threaded cap connector having a hollow needle for coupling (in fluid-flow communication) to a corresponding connector 27 on the reservoir 24. Alternatively or in addition, the reservoir 24 may include a septum as part of the connector 27, for receiving an end of a hollow needle. The opening or port on the base portion 20 may be provided with corresponding connector structure, such as, but not limited to a Luer connector receptacle or a threaded receptacle shaped to receive a threaded cap connector. Other embodiments may employ other suitable connectors or connection arrangements for connecting one end of the tube 25 in fluid-flow communication with the reservoir 24.

The other end of the tube 25 may connected to a hollow needle 21 for piercing the patient's skin and conveying infusion media into the patient. The hollow needle 21 may be secured to the patient's skin, for example, by manual application or with the assistance of an insertion tool, such as, but not limited to the insertion tool described in U.S. Patent Application Publication No. 2002/0022855, titled "Insertion Device For An Insertion Set And Method Of Using The Same." In other embodiments, as described below, a hollow needle and insertion mechanism may be included within the delivery device 12, so as to avoid the need for a port 23, tube 25 and connector 26.

The durable portion 22 of the delivery device 12 includes a housing shell configured to mate with and secure to the disposable base portion 20. The durable portion 22 and base portion 20 may be provided with correspondingly shaped grooves, notches, tabs or other suitable features that allow the two parts to easily snap together, by manually pressing the two portions together in a manner well known in the mechanical arts. In a similar manner, the durable portion 22 and base portion 20 may be separated from each other by manually applying sufficient force to unsnap the two parts from each other. In further embodiments, a suitable seal, such as an o-ring seal, may be placed along the peripheral edge of the base portion 20 and/or the durable portion 22, so as to provide a seal against water between the base portion 20 and the durable portion 22.

The durable portion 22 and base portion 20 may be made of suitably rigid materials that maintain their shape, yet provide sufficient flexibility and resilience to effectively snap together and apart, as described above. The base 20 material may be selected for suitable compatibility with the patient's skin. For example, the base portion 20 and the durable portion 22 of the delivery device 12 may be made of any suitable plastic, metal, composite material or the like. The base portion 20 may be made of the same type of material or a different material relative to the durable portion 22. The base portion and durable portions may be manufactured by injection molding or other molding processes, machining processes or combinations thereof.

For example, the base portion 20 may be made of a relatively flexible material, such as a flexible silicon, plastic, rubber, synthetic rubber or the like. By forming the base portion of a material capable of flexing with the patient's skin, a greater level of patient comfort may be achieved when the base portion is secured to the patient's skin. Also, a flexible base portion 20 can result in an increase in the site options on the patient's body at which the base portion 20 may be secured.

In the embodiment illustrated in FIG. 2, the durable portion 20 of the delivery device 12 is connected to a sensor 14, through a sensor lead 29. The sensor 14 may comprise any suitable biological or environmental sensing device, depending upon the nature of the treatment to be administered by the delivery device 12. For example, in the context of delivering insulin to a diabetes patient, the sensor 14 may comprise a blood glucose sensor.

The sensor 14 may be an external sensor that secures to the patient's skin or, in other embodiments, may be an implantable sensor that is located in an implant site within the patient. In the illustrated example of FIG. 2, the sensor 14 is an external sensor having a disposable needle pad 14' that includes a needle for piercing the patient's skin and enzymes and/or electronics reactive to a biological condition, such as blood glucose level, of the patient. The disposable needle pad 14' may electrically contact electrical conductors in the lead 29, to convey electrical signals from the sensor 14 to suitable sensor electronics located within the durable portion 22 of the delivery device 12. The lead 29 may have any suitable length. In this manner, the delivery device 12 may be provided with sensor data from a sensor secured to the patient, at a site remote from the location at which the delivery device 12 is secured to the patient.

While the embodiment shown in FIG. 2 includes a sensor 14 connected by a lead 29 for providing sensor data to sensor electronics located within the durable portion 22 of the delivery device 12, other embodiments may employ a sensor 14 located within the delivery device 12, as described below. Yet other embodiments may employ a sensor 14 having a transmitter for communicating sensor data by a wireless communication link with to receiver electronics located within the durable portion 22 of the delivery device 12. The wireless connection between the sensor 14 and the receiver electronics in the durable portion 22 of the delivery device 12 may comprise a radio frequency RF connection, an optical connection, or another wireless suitable communication link. Further embodiments need not employ a sensor and, instead, provide infusion media delivery functions without the use of sensor data.

As described above, by separating disposable elements of the delivery device 12 from durable elements, the disposable elements may be arranged on the disposable base portion 20, while durable elements may be arranged within a separable durable portion 22. In this regard, after one (or a prescribed number) of uses of the delivery device 12, the disposable base portion 20 may be separated from the durable portion 22, so that the disposable base portion 20 may be disposed of in a proper manner. The durable portion 22 may, then, be mated with a new (un-used) disposable base portion 20 for further delivery operation with a patient.

The reservoir 24 may be supported by the disposable base portion 20 in any suitable manner. The reservoir may be provided as a cartridge or generally cylindrical canister for containing fluidic infusion media. For example, the base portion 20 may be provided with projections or struts, or a trough feature for holding a cartridge-type reservoir in a manner that allows a user to readily remove the reservoir from the base portion and re-install a new or refilled reservoir, when replacement or re-filling is needed, as described with respect to further embodiments below. Alternatively, or in addition, the reservoir 24 may be secured to the base portion 20 by a suitable adhesive or other coupling structure. The reservoir 24 has a port and may be supported by the base portion 20 in a position at which a connector 26 may engage or otherwise come into fluid flow communication with the reservoir port, when the connector 26 is connected to the port 23 on the base portion 20.

The durable portion 22 of the delivery device 12 may include a motor or other force-applying mechanism, for applying a force to the infusion media within the reservoir 24 to force fluidic infusion media out of the reservoir 24 and into the needle 27, for delivery to the patient. For example, an electrically driven motor may be mounted within the durable portion 22 with appropriate linkage for causing the motor to operably engage a piston of the reservoir and drive the reservoir piston in a direction to cause the fluidic pressure within the reservoir to increase and thereby force fluidic infusion media out of the reservoir port, into the tube 25 and needle 27. The motor may be arranged within the durable portion 22 and the reservoir may be correspondingly arranged on the disposable portion 20, such that the operable engagement of the motor with the reservoir piston (e.g., through appropriate linkage) occurs automatically upon the patient-user snap fitting the durable portion 22 onto the disposable portion 20 of the delivery device 12.

Figure 3:
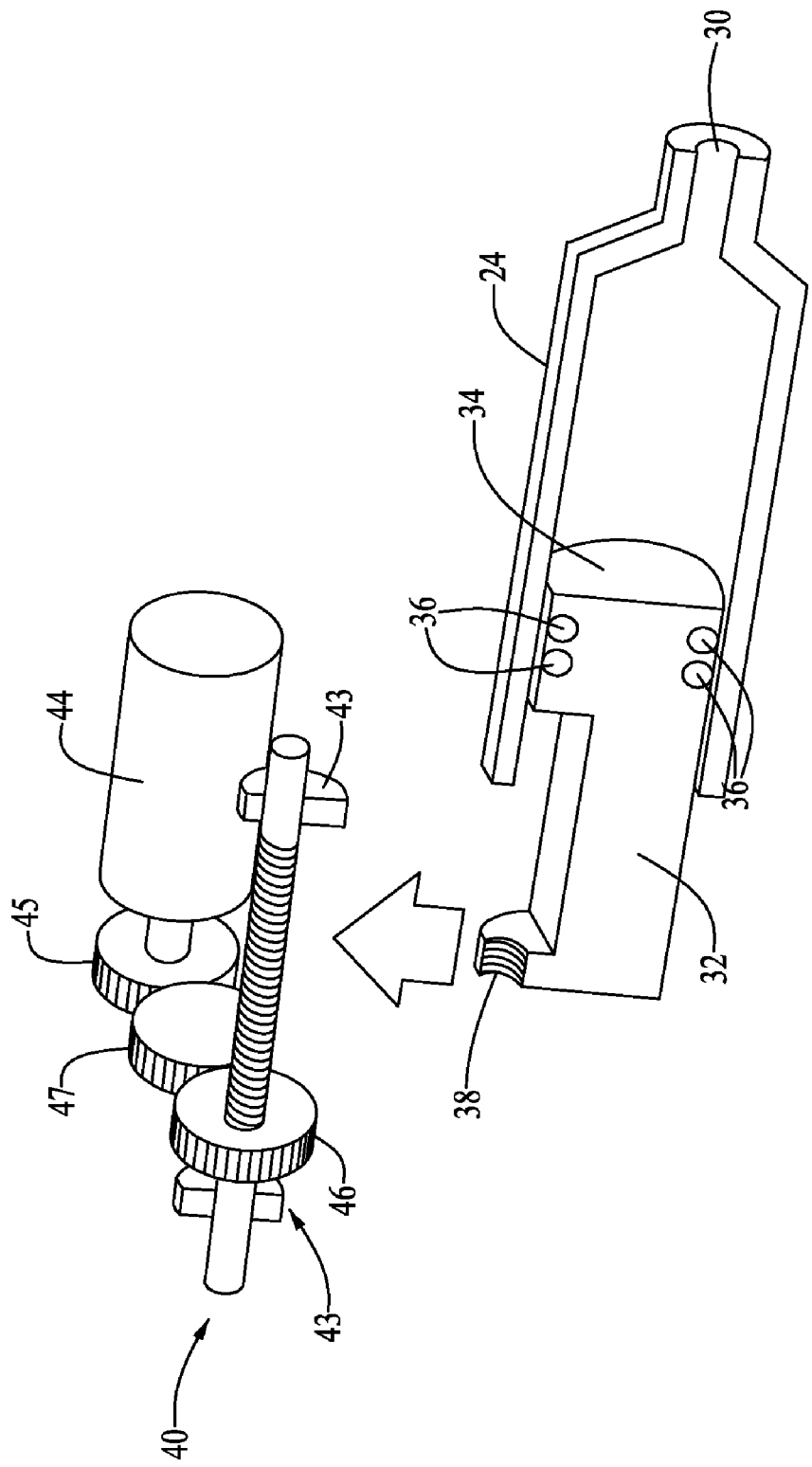

One example of a motor and reservoir configuration is shown in FIG. 3. In the embodiment of FIG. 3, the reservoir 24 (shown in cross-section) comprises a canister, for example, made of a suitable metal, plastic, ceramic, glass, composite material or the like, for containing a fluidic infusion media. The canister reservoir 24 includes an opening 30, through which infusion media from inside of the reservoir may be expelled from the reservoir in response to a force applied by a piston plunger 32. As described in further embodiments below, the opening 30 may contain a septum that is designed to be pierced by a needle.

The piston plunger 32 extends partially into the canister from the opposite side of the canister relative to the opening 30. The piston plunger 32 may be made of a suitably rigid material, such as but not limited to metal, plastic, ceramic, glass or composite material, and has a head 34 that has an outside diameter of slightly less than the inside diameter of the canister portion of the reservoir. One or more seals, such as but not limited to o-ring type seals 36, may be arranged within annular grooves provided on the piston plunger head 34. The o-ring seals 36 may be made of any suitable material, including, but not limited to rubber, plastic, metal, composite material or the like, where such o-rings provide a sealing function for inhibiting the leakage of infusion media from the piston-plunger end of the reservoir 24. The materials from which the reservoir 24, piston plunger 32 and seal(s) 36 are made are preferably selected for suitable strength and durability characteristics, as well as compatibility with the infusion media.

The piston plunger 32 in FIG. 3 includes a keyed or threaded portion 38, located external to the canister reservoir 24. The keyed or threaded portion 38 is provided with keys, key slots or threads that are configured to engage corresponding key slots, keys or threads on a linkage structure 40. In the illustrated example of FIG. 3, the linkage structure 40 includes a keyed, slotted or threaded shaft 42, supported by bearings 43 or other suitable structure for allowing rotation of the shaft 42 about its longitudinal axis. The bearings 43 may be mounted within the durable portion 22 of the delivery device 12, so as to support the shaft 42 for rotation within the durable portion 22.

A motor 44 is mechanically coupled to the shaft 42, to drive the shaft in a rotary motion about its axis in a controlled manner. The motor 44 may be coupled to the shaft 42 through one or more suitable gears, belts, chains, drive shafts or other linkage structure. In the embodiment illustrated in FIG. 3, the motor 44 includes a drive gear 45, while the shaft 42 is provided with a further gear 46. A third gear 47 is arranged between the drive gear 45 and the further gear 46, to convey rotary drive force from the motor 44 to the shaft 42. Thus, the drive gear 45, the further gear 46 and the third gear 47 form a gear train for transferring motor drive force to the shaft 42. In this manner, as the motor rotatably drives the motor drive shaft, the gear train transfers the motor drive force to rotate the shaft 42, which is transferred to an axial movement of the piston plunger 32 relative to the reservoir 24.

The motor 44, shaft 42 and gear train therebetween may be mounted within the durable portion 22 of the delivery device in a location at which the keyed, slotted or threaded portion of the shaft 42 engages the slotted, keyed or threaded portion of the piston plunger 32, as shown in FIG. 3. In this manner, when the durable portion 22 is snap fitted onto the disposable portion 20, the keyed, slotted or threaded portion of the shaft 42 automatically engages the slotted, keyed or threaded portion of the piston plunger 32 without requiring further user manipulation of the elements.

While not shown in FIG. 3, the motor 44 may be provided with electrical terminals for connection to a motor control circuit (not shown). The motor control circuit may be mounted within the durable portion 22 of the delivery device, for controlling the operation of the motor according to a desired infusion delivery program or profile. A delivery program or profile may be stored within a suitable electronic storage medium located within the durable portion 22 and/or may be communicated to the delivery device 12 from other sources, such as a CCD 16 or a computer 18 (as shown in FIG. 1). Alternatively or in addition, the motor control circuit may control the motor to deliver one or more discrete volumes of infusion media in response to delivery demand control signals generated within the device 12 or communicated to the device 12 from other sources, such as a CCD 16 or a computer 18 (as shown in FIG. 1).

In the arrangement illustrated in FIG. 3, once the reservoir 24 has been sufficiently emptied or otherwise requires replacement, the patient-user may simply unsnap and remove the durable portion 22 from the disposable base portion 20 of the delivery device and replace the disposable portion 20 (including the reservoir) with a new disposable portion having a filled or re-filled reservoir 24. The durable portion 22 may be snap fitted onto the new disposable portion and the delivery device (including the new disposable portion) may be secured to the patient's skin, as described above.

In a further embodiment, the reservoir 24 may be supported by the base portion 20 in a manner that allows the reservoir 24 (and piston plunger 32) to be removed from the remainder of the base portion 20 and disposed of or re-filled, and further allows a new or re-filled reservoir 24 (and piston plunger 32) to be re-installed onto the base portion 20, while the base portion remains secured to the patient-user's skin. In this manner, the reservoir may be removed and a new or re-filled reservoir may be installed on the same base portion. The same base portion may be used for multiple new or re-filled reservoirs and, then, disposed of after a prescribed number of new or re-filled reservoirs have been used on the base portion, while the same durable portion may be used for multiple base portion replacements.

The reservoir may be supported on the disposable base portion 20 by a trough structure (or other type of seat) formed on the base portion 20. In such an embodiment, the reservoir may be freely lifted off of the trough structure (or other type of seat) by the patient-user, when the durable portion 22 is removed from the base portion 20 of the delivery device 12, but is inhibited from lifting off of the trough structure by an obstructing part of the durable portion 22 when the durable portion 22 is snap fitted onto the base portion 20. Alternatively, or in addition, other manners of removably supporting the reservoir 24 on the base portion 20 may be employed, including, but not limited to, straps attached to the base portion, low strength adhesive material on the base portion, or the like.

While the embodiment shown in FIG. 3 is one example of a manner of coupling a drive motor 44 to a reservoir 24, to drive infusion media from the reservoir in a controlled manner, other suitable manners of coupling a drive motor 44 to a reservoir 24 may be employed in accordance with other embodiments of the present invention, while still allowing a disposable portion of a delivery device to be easily removable and replaceable relative to a durable portion of the delivery device. Further examples of drive motor coupling arrangements are shown in FIGS. 4-11, wherein components similar to those described above with respect to FIG. 3 are provided with correspondingly similar reference numbers.

The drive motor coupling arrangement of FIG. 4 includes a piston plunger 32 that has a half-nut or single rack configuration. In particular, the piston plunger 32 in FIG. 4 has a threaded rack 48 extending along the longitudinal dimension of the piston plunger, from a location offset from the center of the head 34. The motor 44 includes a rotatably driven drive shaft on which a drive screw 49 is mounted for rotation with the drive shaft. During operation, the drive screw 49 is arranged to engage the threaded rack 48 and, upon rotation of the drive screw, provides an linear movement of the piston plunger 32 relative to the reservoir 24.

The reservoir 24 in FIG. 4 may be supported on a base portion 20 of the delivery device 12 (FIG. 1), in a manner as described above with respect to FIG. 3. Similarly, the motor 44, including the drive shaft and drive screw 49 may be supported within the durable portion 22 of the delivery device 12. When the durable portion 22 is removed from the base portion 20, the rack 48 may be easily disengaged from the drive screw 49 by simply lifting the reservoir off of the base portion 20. A new or re-filled reservoir (and piston plunger 32) may be re-installed onto the base portion 20 and readily engaged with the drive screw 49, by simply aligning the threaded rack 48 with the drive screw 49 while placing the new or re-filled reservoir onto the base portion 20. A trough or seat may be included in the base portion 20, as described above, in a location that aligns the threaded rack 48 with the drive screw 49, when the durable portion 22 of the delivery device is snap fitted onto the base portion 20 of the delivery device.

A further drive motor coupling arrangement is shown in FIG. 5, wherein the piston plunger 32 has a threaded rack 48 extending along the longitudinal dimension of the piston plunger, from a location offset from the center of the head 34, similar to the threaded rack 48 in FIG. 4. However, in the arrangement shown in FIG. 5, the motor 44 is arranged such that the drive shaft of the motor is perpendicular to the longitudinal, axial dimension of the piston plunger 32. The drive shaft of the motor 44 in FIG. 5 is provided with a pinion gear 50 that engages the threaded rack 48 of the piston plunger 32. In this manner, as the motor rotatably drives the motor drive shaft, the pinion gear 50 rotates with the motor drive shaft to provide a linear movement of the piston plunger 32 relative to the reservoir 24.

The reservoir 24 in FIG. 5 may be supported on a base portion 20 of the delivery device 12 (FIG. 1), in a manner as described above with respect to FIG. 3 and 4. Similarly, the motor 44, including the drive shaft and pinion gear 50 may be supported within the durable portion 22 of the delivery device 12. When the durable portion 22 is removed from the base portion 20, the rack 48 may be easily disengaged from the pinion gear 50 by simply lifting the reservoir off of the base portion 20. A new or re-filled reservoir (and piston plunger 32) may be re-installed onto the base portion 20 and readily engaged with the pinion gear 50, by simply aligning the threaded rack 48 with the pinion gear 50 while placing the new or re-filled reservoir onto the base portion 20. A trough or seat may be included in the base portion 20, as described above, in a location that aligns the threaded rack 48 with the pinion gear 50 when the durable portion 22 of the delivery device is snap fitted onto the base portion 20 of the delivery device.

Figure 7:
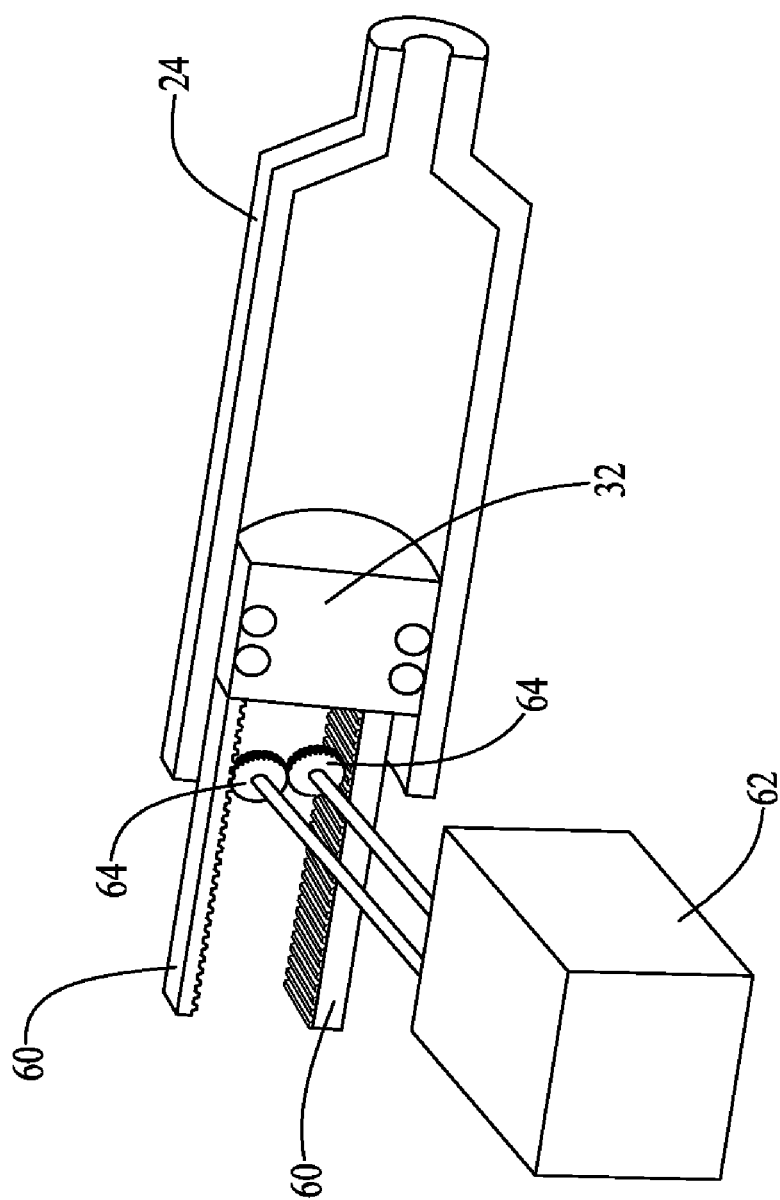

A further drive motor coupling arrangement is shown in FIG. 6. The arrangement in FIG. 6 is similar to that of FIG. 5, except that the piston plunger 32 is provided with a double rack arrangement composed of two racks 60 as described above with respect to rack 48. In addition, the motor 62 in FIG. 5 is provided with two drive shafts, each drive shaft having a pinion gear 64 for engaging the racks 60 and operates in a manner similar to the single rack and pinion arrangement of FIG. 5. In the arrangement shown in FIG. 6, the pinion gears 64 are arranged side-by-side, along the longitudinal or axial direction of the piston plunger 32. FIG. 7 shows a configuration similar to FIG. 6, except that the pinion gears 64 are arranged adjacent each other along a direction perpendicular to the longitudinal or axial direction of the piston plunger 32.

Yet a further drive motor coupling arrangement is shown in FIG. 8. The arrangement of FIG. 8 is similar to that of FIG. 4, except that the piston plunger 32 is provided with a hollow shaft portion 80 having a threaded interior. The drive screw 49 is configured to be threadably inserted into the hollow shaft portion 80, such that threads on the drive screw engage threads on the inner surface of the hollow shaft 80. In this manner, rotation of the drive shaft and drive screw 49 by the motor 44 provides a linear movement of the piston plunger 32 within the reservoir 24. In the embodiment shown in FIG. 8, one or more seals 80, such as o-ring seals 82, may be arranged around the hollow shaft portion 80.

A further drive motor coupling arrangement is shown in FIGS. 9 and 10, wherein the motor 44 is provided with a threaded drive shaft screw 90. The arrangement of FIGS. 9 and 10 includes a piston plunger 92 having a piston head 34 similar to the piston head described above with respect to FIGS. 4-8. However, the piston plunger 92 in FIGS. 9 and 10 further includes a pair of arm members 94 that extend from the head 34 in a V configuration. Each arm member 94 includes a threaded foot portion 96 extending toward the threaded drive shaft screw 90.

The arm members 94 are connected to or otherwise extended from the piston head 34 in a manner that allows the arm members 94 to pivot slightly in the direction toward and away from the threaded drive screw 90. By virtue of their pivoting motion, the arm members 94 may be pivoted such that the threaded foot portions 96 are brought into or out of engagement with the threaded drive screw 90. When the arm members 94 are pivoted such that the foot portions 96 are out of engagement with the threaded shaft 90, as shown in FIG. 9, the reservoir 24 may be separated from the motor 44 and removed from the delivery device 12. However, when the arm members 94 are pivoted such that the foot portions 96 are brought into engagement with the threaded drive screw 90, as shown in FIG. 10, then rotation of the threaded drive screw by the action of the motor 44 will result in a linear movement of the piston head 34 within the reservoir 24.

A pair of cam surfaces 98 may be arranged within the drive device 12 at locations that engage the outer surface of the arm members 94, when the reservoir 24 and piston plunger are rotated, for example, in the direction of the arrow 99 in FIG. 9. The cam surfaces 98 may be arranged relative to the reservoir 24, such that engagement of the arm members 94 with the cam surfaces 98 causes the arm members 94 to pivot toward the threaded drive screw to engage the foot portions 96 with the threaded drive screw. The cam surfaces 98 may be formed as part of the structure of the base portion 20, the durable portion 22 or both.

Accordingly, during a reservoir canister replacement or refilling operation, a patient-user may remove the durable portion 22 from the base portion 20 of the delivery device to expose the reservoir canister 24. The patient-user may, then, rotate the reservoir 24 in a direction to disengage the arm members 94 from the cam surfaces 98 and allow the foot portions 96 of the arm members 94 to disengage from the threaded drive shaft 90 (as shown in FIG. 9). In that position, the reservoir 24 (including the piston plunger and arm members 94) may be lifted from the base portion and either re-filled or replaced with a new reservoir cartridge 24 (including piston plunger and arm members 94). The new or re-filled reservoir cartridge may be placed back into the base portion 20 with the arm members 94 arranged out of engagement with the cam surfaces 98 (as shown in FIG. 9). Thereafter, the patient-user may rotate the reservoir cartridge 24 in the direction of arrow 99, to bring the arm members 94 into engagement with the cam surfaces 98 and cause the foot portions 96 to engage the threaded drive shaft 90 (as shown in FIG. 10).

Figure 11:
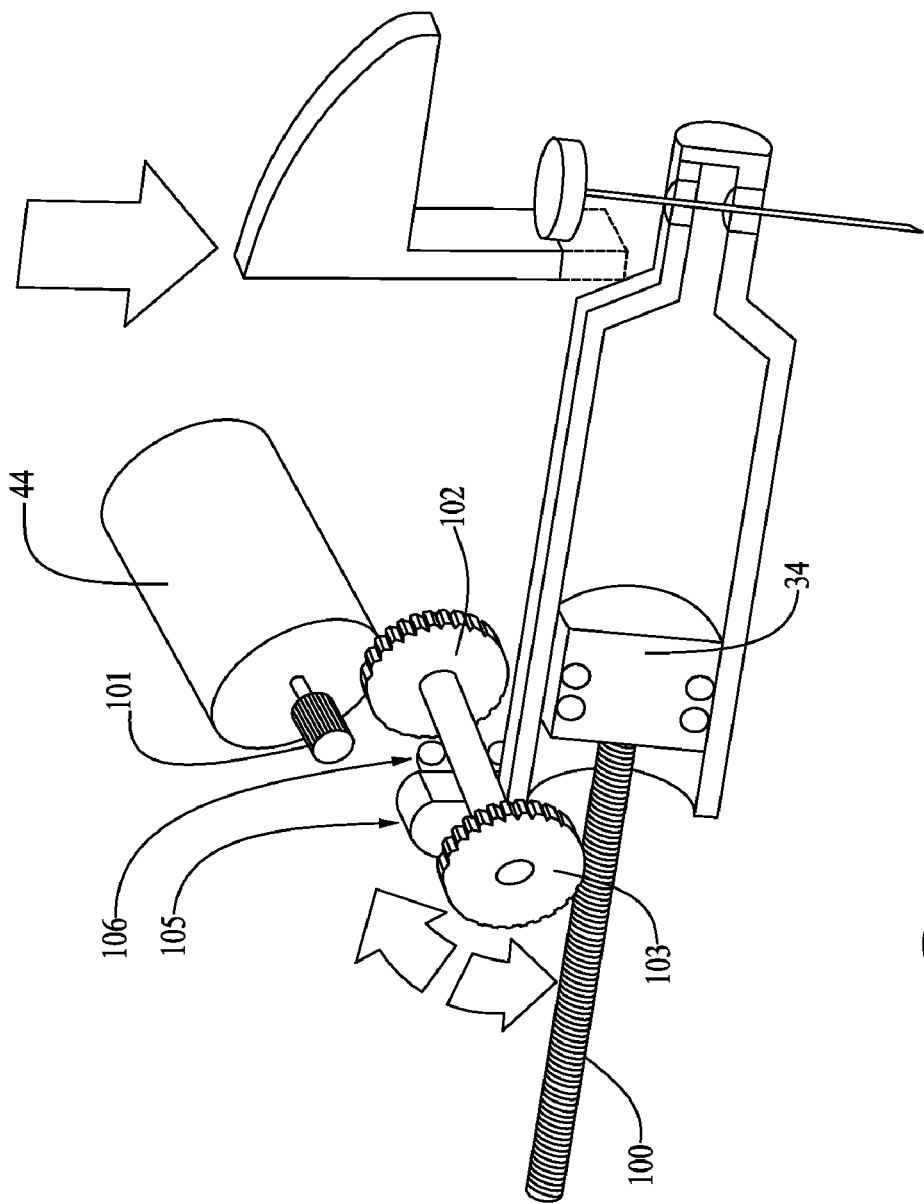

A further drive motor coupling arrangement is shown in FIG. 11. The coupling arrangement in FIG. 11 is similar to that of FIG. 3, except that the threaded portion of the piston plunger comprises a threaded screw 100 extending from the piston head 34 and engaging a gear of the gear train. In particular, the gear train in the embodiment of FIG. 11 includes a motor drive gear 101, a gear 102 engaging the motor drive gear and a shaft 104 coupling the gear 102 to a third gear 103. The third gear 103 is arranged to engage the threaded screw 100 such that rotation of drive gear 101 by the motor 44 causes rotation of the gears 102 and 103, which causes a linear movement of the shaft 100 and piston head 34 relative to the reservoir 24. The shaft 104 may be supported by one or more bearing structures 105 and may include one or more seals, such as o-ring seals. 106.

The shaft 104 may be configured to rigidly connect gears 102 and 103, such that rotation of the gear 102 by the drive gear 101 results in a like rotation of the gear 103. Alternatively, the gear 103 may be coupled to the shaft 104 with a ratchet connection that allows the gear to be driven in one direction (such as the direction in which the piston head 34 would be moved toward the septum end of the reservoir to increase pressure within the reservoir and cause infusion fluid to be expelled from the septum end of the reservoir (provided the septum of the reservoir has been opened). On the other hand, the ratchet connection of the gear 103 with the shaft 104 may allow the gear 103 to freely rotate in the other direction (the direction for causing the piston head 34 to move in the outward direction away from the septum end of the reservoir).

Thus, as described above, various arrangements for connecting a drive motor 44 to a reservoir cartridge 24 may be employed to allow fluidic media within the reservoir cartridge to be delivered to a patient in a controlled manner. The arrangements described above include a piston plunger 32 for imparting a controlled force on the fluidic media within the reservoir 24, in response to the controlled drive force of a motor. However, other embodiments may employ other suitable arrangements for imparting a controlled force on the fluidic media, including arrangements in which a rotary pump blade is mounted within or to the reservoir cartridge 24.

Figure 12:
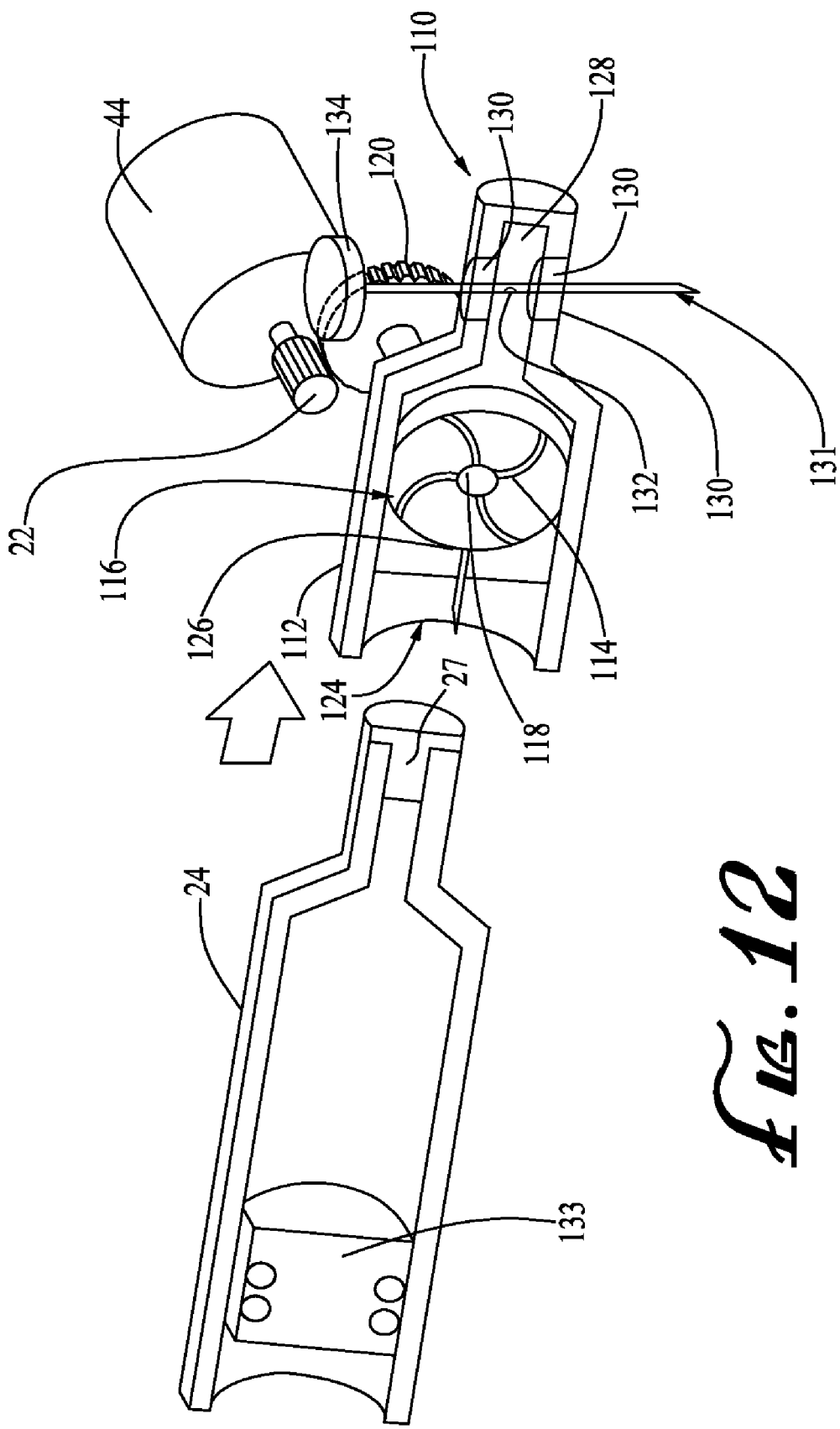

For example, FIG. 12 shows a cross-sectional view of an embodiment of a pump assembly 110 for connection to a septum end of a reservoir cartridge, 24. The pump assembly 110 includes a housing portion 112 that contains a pump chamber 114. A rotary pump blade 116 is supported for rotation on a drive axle 118, within the pump chamber 114. The drive axle 118 passes through a sealed opening in the side of the housing 112 and is attached to a gear 120 located outside of the housing 112. The gear 120 is engaged with a motor drive gear 122 coupled to the drive shaft of the motor 44, such that rotation of the motor drive shaft by the motor 44 causes the gear 120 to drive the blade 116 in a rotary motion within the pump chamber 114.

The housing 112 includes a receptacle 124 for having a size and shape for receiving the septum end of a reservoir cartridge 24. A hollow needle 126 is arranged with a sharp end located within the receptacle 124 and facing toward the open end of the receptacle 124. The opposite end of the hollow needle is provided in fluid flow communication with the pump chamber 114. The pump chamber 114 is also provided in fluid flow communication with an outlet chamber in an outlet end 128 of the housing 112.

The outlet end 128 of the housing 112 may include a port or other suitable opening to convey fluidic material out of the outlet chamber end 128. In the embodiment shown in FIG. 12, the outlet end 128 of the housing 112 includes a pair of septa 130 arranged to allow a needle to pass through both septa 130. In this manner, a hollow needle 131 may be pushed through the septa 130 to align an inlet port 132 on the needle in fluid flow communication with the outlet chamber. The hollow needle 131 thereby provides a fluid flow path for the fluid within the outlet chamber end 128 of the housing 112 to exit the outlet chamber.

Thus, according to the arrangement shown in FIG. 12, a pump assembly 110 may be coupled to a reservoir 24, by pushing the receptacle end 124 of the pump assembly housing 112 over the septum end of the reservoir cartridge 24 until the hollow needle 126 pierces the septum 27 on the reservoir cartridge 24 and extends partially into the reservoir. As a result, the interior of the reservoir 24 will be in fluid flow communication with the pump chamber 114. Thereafter, rotation of the pump blade 116 in a forward pumping direction will produce a negative pressure to draw fluid from the reservoir, through the hollow needle 126 and into the pump chamber.

The action of the pump blade further causes fluid to be expelled from the pump chamber 114 and into the outlet chamber end 128 of the housing 112, where the fluid is caused to flow into the needle port 132 and through the needle 131. As fluidic infusion media is pumped out of the reservoir 24, a moveable plunger 133 within the reservoir 24 may be caused to move toward the septum end of the reservoir by the negative pressure imparted by the pump assembly 110. The plunger 133 may be configured similar to the piston plunger head 34 described above and may include one or more seals, such as o-ring seals, as described above with respect to the piston plunger head 34. After the reservoir 24 has been sufficiently spent, the pump assembly housing 112 may be disengaged from the reservoir 24 by simply pulling the reservoir 24 and housing 112 apart to disengage the needle 126 from the septum 27.

In the arrangement shown in FIG. 12, the needle 131 may be used in place of the needle 21, tube 25 and connector 26 shown in FIG. 2. In particular, a reservoir 24 may be supported on a base member 20, as described above and a pump assembly 110 may be connected to the reservoir 24, as described above with respect to FIG. 12. The base portion 20 may be provided with an opening or pierceable wall in alignment with the tip of the needle 131, to allow the needle to pass through the base member 20 and into the patient-user's skin under the base member 20, when extended. In this manner, the needle 131 may be used to pierce the patient-user's skin and deliver infusion media to the patient.

Alternatively, the needle 131 may be extended through a hollow cannula, such that upon piercing the patient-user's skin with the needle, an end of the hollow cannula is guided through the patient's skin by the needle 131. Thereafter, the needle 131 may be removed, leaving the hollow cannula in place, with one end of the cannula located within the patient and the other end of the cannula located in the outlet chamber end 128 of the pump assembly 110, to convey pumped fluid from the pump assembly 110 into the patient.

The needle 131 may be provided with a head 134 having a surface on which a force may be applied (downward directed force with respect to the orientation in FIG. 12), to move the needle 131 through the septa 130 and into the patient's skin. The force may be applied to the needle head 134 by manually pushing the needle head. For example, a patient-user may secure the base member 20 to an appropriate location on the patient-user's skin. With the reservoir 24 and pump assembly 110 supported on the base member as described above, the patient-user may apply a force onto the needle head 134 to extend the needle 131 (or needle and cannula) through the septa 130, through the base portion 20 and into the patient-user's skin. The durable portion 22 (containing the motor 44 and drive gear 122) may be snap fitted to the base portion 20 in a position in which the motor 44 is aligned with the gear 120 on the reservoir 24. The motor 44 may be controlled by motor control electronics located within the durable portion 22 to drive the rotary pump blade to pump fluidic infusion media from the reservoir 24, through the needle 131 (or cannula) and into the patient in a controlled manner, for example, according to delivery instructions or a predefined delivery program or profile.

Other suitable arrangements for supporting a reservoir 24 on a base portion 20, coupling a needle (or cannula) to the reservoir and inserting the needle (or cannula) into a patient-user's skin are shown in FIGS. 13-24 and 28-30. Elements in FIGS. 13-24 and 28-30 that are similar to those described above with respect to FIGS. 1-12 are numbered with correspondingly similar reference numbers.

For example, FIG. 13 shows a partially exploded view of some of the components of a delivery device 10, including a disposable base portion 20, a durable portion 22 and a reservoir 24 as described above. The pump, motor, linkage and electronics are not shown in FIG. 13, to simplify the drawing. The reservoir 24 in FIG. 13 is supported in a disengaged position on the base by a trough-like structure 140. The trough 140 is positioned on a plurality of struts 142 (two on each side for a total of four in the embodiment of FIG. 13). The struts 142 are relatively rigid, but have sufficient flexibility and resilience to allow the struts to provide a snap fit with the trough, as described below. The struts 142 may be formed integral with the base portion 20 or may be separate elements that are attached to the base portion 20 by any suitable attachment mechanism. The struts 142 may be made of any suitable material, including but not limited to the material of the base 20, metal, plastic, composite material or the like.

With reference to FIG. 14, each strut 142 has a surface 144 on which the trough structure 140 (FIG. 13) rests, when in a disengaged position. In the illustrated embodiment, the surface 144 is angled to enhance the ability of the trough structure 140 to move into an engaged position (as described below with reference to FIG. 16). In other embodiments, the surface 144 may have a curvature or other suitable shape that allows the trough structure 140 to move into an engaged position. Each strut 142 also has a stop surface 146, for abutting an edge surface 148 of the trough structure 140, upon the trough structure 140 being moved into an engaged position (as shown in FIG. 16).

The trough-like structure 140 includes a platform portion 150 abutted by a spring 152. The spring 152 may comprise a coil spring arranged between the base 20 and the platform portion 150, to bias the platform portion 150 toward the disengaged position (as shown in FIG. 13). A hollow needle 154 is secured to and extended through the platform portion 150, such that one end of the needle 154 is directed toward the septum end of a reservoir canister 24, when the reservoir canister 24 is placed in the trough-like structure 140. The opposite end of the needle 131 is directed toward the disposable base 20. The disposable base 20 may include an opening or pierceable wall portion in alignment with the needle end directed toward the base 20, to allow the needle end to pass through the base 20 and into the patient-user's skin, when the reservoir and trough-like structure is moved into an engaged position.

More specifically, with the configuration of FIGS. 13-16, a patient-user may secure the disposable base portion to the patient-user's skin, as described above. A reservoir canister 24 having a septum end 27 is arranged on the trough-like structure 140, with the septum 27 in alignment with the exposed end (upward facing end in FIG. 13) of the needle 154. By manually pressing the reservoir canister 24 toward the disposable base 20, the trough-like structure 140 may be moved from its position shown in FIG. 13, toward the base 20 and into the engaged position shown in FIG. 16, against the force of the spring 152. During movement of the trough-like structure 140 between the disengaged position (FIG. 13) and the engaged position (FIG. 16), the struts 142 flex slightly to allow the trough-like structure to move to a position under the stop surfaces 146 of the struts 142. When in the engaged position (FIG. 16), the stop surfaces 146 of the struts 142 engage the edge surfaces 148 of the trough-like structure 140, to lock the trough-like structure in an engaged position.

The action of moving the reservoir canister 24 into an engagement position also effects the placement of the needle 154 into an engagement position. Initially, the end of the reservoir end of the needle 154 may be arranged adjacent or even partially extended into the septum 27 of the reservoir canister 24. By manually engaging or pressing the reservoir canister 24 onto the trough-like structure 140, the hollow needle 154 is caused to pierce the septum 27 of the reservoir canister 24 and come into flow communication with fluidic media within the reservoir canister 24. By applying a greater manual pressure onto the reservoir canister 24, the reservoir canister 24 and the trough-like structure 140 are caused to move from the disengaged position (FIG. 13) into the engaged position (FIG. 16). At the same time, the needle 154 is moved with the trough-like structure 140, to cause the lower end of the needle to pass through the base portion 20 and into the patient-user's skin.

When the trough-like structure 140 reaches the engaged position (FIG. 16), the struts 142 snap into position over the edge 148 of the trough-like structure 140. Thus, in the engaged position (FIG. 16), the spring 152 is compressed, the trough-like structure 140 is locked in place by the struts. In addition, when in the engaged position, the hollow needle 154 is located with one end of the needle in fluid flow communication with the interior of the reservoir canister 24 and the other end of the needle inserted into the patient, as shown in FIG. 15. Once the reservoir canister 24 and trough-like structure 140 are in the engaged position (FIG. 16), the durable portion 22 may be snap fitted to the base portion 20 so as to engage a motor with the reservoir canister 24 for driving fluid from the reservoir canister 24 in a controlled manner, as described above.

FIGS. 17 and 18 show another configuration example for moving a hollow needle (or cannula) into an engagement position, in which the needle (or cannula) is in flow communication with the reservoir canister 24 and has an end located within the patient-user.

In the configuration shown in FIGS. 17 and 18, a spring-biased needle 170 is surrounded by a coil spring 172 and extends from a spring head member 174. When the spring 172 is compressed (as shown in FIG. 17), the needle 170 is in a retracted position in which the sharp end of the needle is positioned adjacent (or even slightly piercing) the septum end 27 of a reservoir canister 24. When the spring 172 is in the uncompressed or partially uncompressed state (as shown in FIG. 18), the needle 170 is moved through the septum 27 of the reservoir canister 24, through the base portion 20, and into a patient-user's skin.

The disposable base portion 20 may be provided with one or more latch members 176 that may be positioned to abut the spring head member 174, when the spring 172 is in the retracted position, to hold the spring 172 (and needle 170) in the retracted position shown in FIG. 17. The latch member(s) 176 may be manually moveable or flexible to selectively disengage from the spring head member 174 and allow the spring to expand and move the needle 170 into the extended or engaged position of FIG. 18. The needle 170 may comprise a hollow needle having a side port located in a position that comes into flow communication with the inside volume of the reservoir canister 24 when the needle 170 is positioned in the extended or engaged position (FIG. 18). Alternatively, a cannula may be positioned on the needle 170 such that moving the needle into the extended or engaged position (FIG. 18) moves one end of the cannula into flow communication with the interior of the reservoir canister 24 and the other end of the cannula into the patient-user. Thereafter, the needle 170 may be removed, leaving the cannula in place.

In one example, each latch member 176 may comprise a pivotal member that is supported on a strut or other support structure (not shown) of the base portion 20 for pivotal motion between a latched position (FIG. 17) and an unlatched position (FIG. 18). Each latch member 176 may have a manually operable portion 178 that is arranged to allow a user to selectively apply a manual force to selectively disengage the latch member 176 from the spring head member 174. In the embodiment of FIGS. 17 and 18, two latch members 176 are provided, such that the patient-user must release both latch members 176 at the same time to cause the spring 172 and needle 170 to move from the retracted position (FIG. 17) to the extended or engaged position (FIG. 18).

Yet another configuration example for moving a hollow needle (or cannula) into an engagement position is shown with respect to FIGS. 19-22. In the configuration shown in FIGS. 19-22, the reservoir canister 24 is provided with a head section 190 having an internal flow passage 192 and a septum 194. The internal flow passage 192 has one end in fluid flow communication with the interior of the reservoir canister 24. A spring-biased needle 196 is surrounded by a coil spring 198 and extends from a spring head member 199. When the spring 198 is compressed (as shown in FIG. 19), the needle 196 is in a retracted position in which the sharp end of the needle is positioned adjacent (or even slightly piercing) the septum 194 of a reservoir canister 24. When the spring 198 is in the uncompressed or partially uncompressed state (as shown in FIGS. 20 and 21), the needle 196 is moved through the septum 194 of the reservoir canister 24, through a portion of the flow passage 192, through the base portion 20, and into a patient-user's skin.

A latch member 200 has a catch hook or surface 202 that may be positioned to abut the spring head member 199, when the spring 198 is in the retracted position, to hold the spring 198 (and needle 196) in the retracted position shown in FIG. 19. The latch member 200 may be manually moveable to selectively disengage the catch surface 202 from the spring head member 199 and allow the spring to expand and move the needle 196 into the extended or engaged position of FIGS. 20 and 21. The needle 196 may comprise a hollow needle having a side port located in a position that comes into flow communication with the flow passage 192 and, thus, the inside volume of the reservoir canister 24, when the needle 196 is positioned in the extended or engaged position (FIGS. 20 and 21). Alternatively, a cannula may be positioned on the needle 196 such that moving the needle into the extended or engaged position (FIGS. 20 and 21) moves one end of the cannula into flow communication with the interior of the reservoir canister 24 and the other end of the cannula into the patient-user. Thereafter, the needle 196 may be removed, leaving the cannula in place.

The latch member 200 in FIGS. 19-22 is supported for rotation movement on the reservoir canister head 190. The latch member 200 may connect to or include a valve portion 204 located within the flow passage 192. In the illustrated embodiment, the valve portion 204 comprises a rotary valve having a pass-through passage that aligns with the flow passage 192, when the valve portion 204 is rotated into an open position (ash shown in FIGS. 20 and 21). However, when the valve portion 204 is rotated into a closed position (as shown in FIG. 19), the pass-through passage in the valve portion 204 is not aligned with the flow passage 192 (and, instead, a solid wall of the valve portion 204 blocks the flow passage 192), such that fluid flow from the reservoir canister 24 is inhibited. The latch member 200 may include a handle 206 that allows a patient-user to readily rotate the latch member between the positions shown in FIGS. 19 and 21. The latch member 200 may be separable from the valve portion 204, such that, once the valve member 204 is rotated into an open position (FIG. 20), the latch member 200 may be further rotated to lock the valve member 204 into the open state and to detach the latch member 200 from the valve member 204 (as shown in FIG. 21).

Thus, according to the configuration shown in FIGS. 19-22, a patient-user may secure the disposable base portion 20 onto the patient-user's skin. The patient-user then may grip the handle 206 and rotate the latch member 200 from a position as shown in FIG. 19 into a position as shown in FIG. 20, for example, by turning the handle 206 in the direction of arrow 208. As the latch member 200 is rotated, the catch 202 is caused to align with a notch 210 in the spring head 199 and releases the spring head 199. Upon release of the spring head 199, the spring 198 causes the spring head 199 and needle 196 (or needle 196 and surrounding cannula) to move into the extended or engaged position (shown in FIG. 20). As the needle 196 moves to the extended position (FIG. 20), the needle is passed through the septum 194, a portion of the flow passage 192, the base member 20 and a the patient-user's skin in a single, quick motion.

The patient-user may, then, rotate the handle 206 further in the direction of arrow 212 into a lock position as shown in FIG. 21. In the locked position, the latch member 200 becomes disengaged from the valve member 204. If the needle 196 is used as an introducer needle, for introducing a cannula, the needle 196 may be removed, once the cannula has been set in place. Thus, after rotating the latch member 200 into the position shown in FIG. 21, the latch member (including the introducer needle 196) may be pulled out of the delivery device and disposed of (as shown in FIG. 22).

In one embodiment, the latch member 200 may be accessible to the patient-user, when the durable portion 22 is removed from the base portion 20 of the delivery device 12. In other embodiments, the latch member 200 may extend through an opening in the durable portion 22 so as to be accessible to a patient-user after the durable portion 22 has been fitted onto the base portion 20, as shown in FIG. 22.

Yet other embodiments may employ a more simplified manner of positioning a needle (or needle and cannula) into the extended or engaged position discussed above. For example, FIGS. 23 and 24 show an arrangement similar to that of FIG. 11, except that a simple needle hub member that extends through the durable portion 22 is used. In the configuration of FIGS. 23 and 24, a needle hub comprises a needle 220 for piercing a septum of a reservoir canister 24 as described above. The durable portion 22 of the delivery device 12 is provided with an opening 222 through which the needle 220 may be inserted. The opening 222 is aligned with the septum of the reservoir canister 24 (not in view in FIGS. 23 and 24) located on the disposable portion 20 of the delivery device 12.

The needle 220 may comprise a hollow needle having a side port located in a position that comes into flow communication with the interior of the reservoir canister 24 (not in view in FIGS. 23 and 24) when the needle 220 is positioned in the extended or engaged position (FIG. 23). Alternatively, a cannula may be positioned on the needle 220 such that moving the needle into the extended or engaged position (FIG. 23) moves one end of the cannula into flow communication with the interior of the reservoir canister 24 and the other end of the cannula into the patient-user. Thereafter, the needle 220 may be removed, leaving the cannula in place (as shown in FIGS. 24).

Various aspects of the multiple embodiments described above may be employed independently or in combinations thereof. For example, any one of the various configurations described herein for coupling a motor 44 to a reservoir 24 to drive fluid from the reservoir in a controlled manner may be employed with any one of the various configurations described herein for moving a needle into an engagement position to effect a flow communication between the reservoir 24 and the patient-user.

Significant advantages can be obtained from various embodiments and combinations described herein, wherein a delivery device includes a disposable portion that secures to a patient-user's skin and holds components that come into contact with the infusion media (such as the reservoir), and a durable portion that includes a drive motor and suitable electronics. Expensive components contained in the durable portion of the delivery device may be used over again, while the disposable portion of the delivery device may be readily disposed of after one (or a prescribed number) of uses. By simplifying the manner in which the disposable portion of the delivery device can be replaced and by simplifying the manner in which the delivery device can be re-activate after replacing a disposable portion, a greater number of patients will be able to use and benefit from such delivery devices To further simplify the use and operation of delivery devices as described herein, such delivery devices may be configured in a manner to simplify the ability to remove the disposable base portion 20 from the patient-user's skin. In the examples described above, the disposable base portion 20 may be secured to a user's skin by use of a suitable adhesive. However, if the adhesive is very strong, the patient-user may have difficulty (and, even, pain) when trying to pull or peal the base portion 20 off of the patient-user's skin. Accordingly, in one embodiment, the adhesive applied to the skin-contacting surface of the disposable base portion 20 is provided in selective locations (instead of across the entire surface). Such locations may be selected to provide suitable adhering qualities, such as locations around the position at which the needle passes through the base portion 20.

Alternatively, or in addition, adhesive material may be applied to peripheral regions of the base portion 20, while leaving some or all of the central region of the base portion 20 free of adhesive. One example of an adhesive pattern on the bottom (skin-facing) surface of the base portion 20 is shown in FIG. 25. In FIG. 25, an adhesive pattern is shown in cross-hatching and includes adhesive 230 disposed along the outer peripheral edge of the base portion 20 and further adhesive 232 around a needle opening 234 in the base portion. However, a large part of the central region 236 of the base portion 20 is free of adhesive. In this regard, once a patient-user is able to remove or peal off an edge of the base portion 20 from the patient-user's skin, the rest of the base portion 20 can be pealed off of the skin with reduced force relative to a base portion 20 that is fully covered with adhesive.

In yet a further embodiment, an agent may be applied to dissolve the adhesive or otherwise reduce the adhering qualities of the adhesive, as part of a procedure for removing a base portion 20 from a patient-user's skin. The particular adhesive releasing agent employed may depend upon the type of adhesive and, in some contexts, may be water or an aqueous solution. The releasing agent may be formed in a gel, so as to avoid excessive running of the agent, when it is applied. The agent may be applied in various manners, including a spray applicator. In the configuration shown in FIG. 26, the delivery device 12 is provided with a reservoir 260, such as a flexible container or bladder, containing an adhesive releasing agent. The reservoir 260 may be mechanically coupled to an actuator button 262 that may be manually operated (e.g., pressed) to apply pressure onto the flexible container or bladder 260 to cause the agent within the container 260 to be released.

A network of tubes or conduits 264 may be connected to an outlet opening on the container or bladder 260, to direct the adhesive releasing agent to appropriate dispensing locations around the base portion 20, upon application of a suitable pressure on the container or bladder 260. The base portion 20 may be provided with openings or may be suitably porous to allow releasing agent from the network of tubes or conduits 164 to pass through the base portion 20 to act upon adhesive material disposed between the base portion 20 and the patient-users skin. In embodiments in which the adhesive material is provided in specified locations (as shown in FIG. 25), the network of tubes or conduits 264 may be configured to direct the releasing agent to those specified locations. For example, in connection with the adhesive pattern shown in FIG. 25, a network of tubes or conduits 164 may be configured to dispense the adhesive releasing agent to the outer peripheral edges of the base portion 20 and to an area surrounding the needle opening 234 in the base portion 20.

In further embodiments, the base portion 20 may be made of a relatively flexible material, such as, but not limited to, a silicon rubber, flexible plastic, or the like, wherein the flexible nature of the material allows a patient-user to more easily peal off the base portion 20 from the patient-user's skin. In particular, with a flexible base portion 20, the patient-user may peal off an edge of the base portion 20 from the patient-user's skin and, then bend the edge upward and across the rest of the base portion 20, to provide a pull surface for pealing the remainder of the base portion 20 off of the patient-user's skin.

In this manner, the base portion 20 may be readily pealed off of the patient-user's skin and disposed of, after a suitable period of use. The durable portion 22 of the delivery device 12 may be snap fitted to a new base portion 20 to continue the patient-user's treatment. As described above, the durable portion 22 may contain components, such as the drive motor 44, linkage components for linking the drive motor to a reservoir, and electronics for controlling the drive motor to provide a controlled delivery of infusion media. The drive motor 44 may be any suitable motor that may be electronically controlled, including, but not limited to a stepper motor, brushless motor, or the like.

Figure 27:
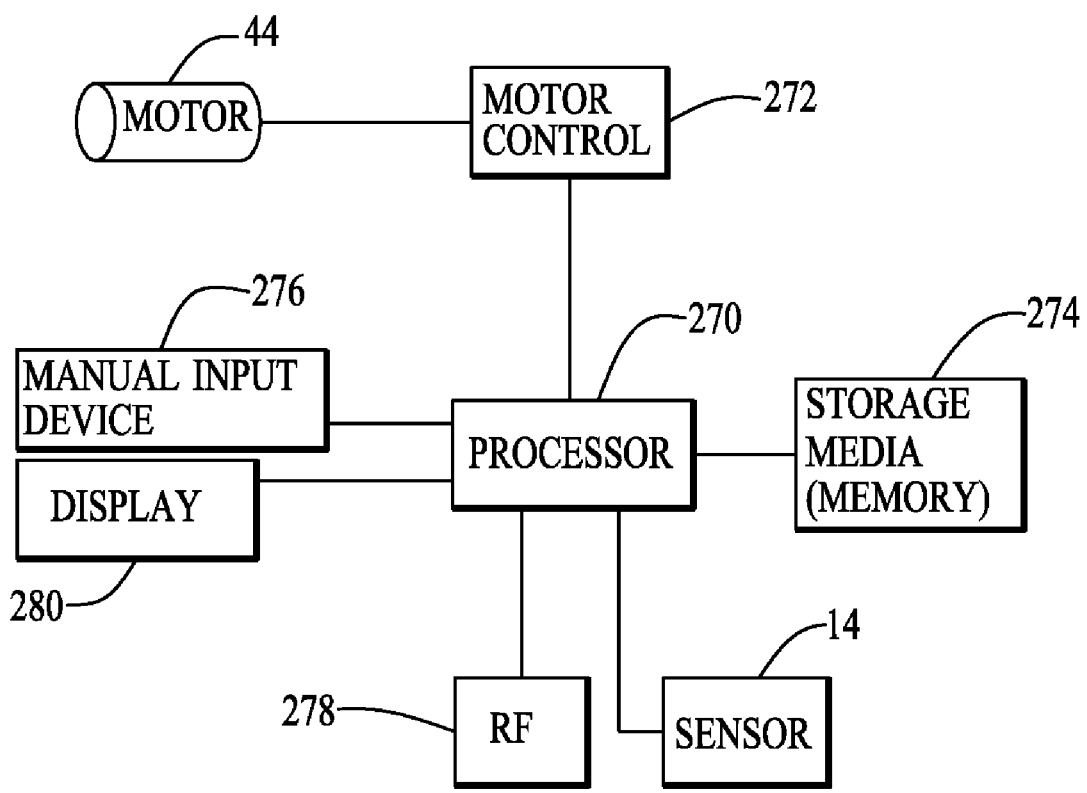
FIG. 27 is a generalized diagram of an electronic system included in a delivery device according to an embodiment of the present invention.

While the electronics for operating the delivery device 12 may take various forms, one example embodiment of an electronics system 270 is shown in FIG. 27, wherein a processor 271 is configured or otherwise programmed to provide functions described herein. The processor 271 may be electronically connected to a motor control circuit 272 for controlling the operation of the motor 44. The motor 44 may be controlled to operate (drive fluid from the reservoir) in accordance with delivery program or profile data stored in an electronic storage device 274 connected to or otherwise associated with the processor 271. Alternatively or in addition, the processor 271 may respond to manual inputs, for example, from a manually operated button or other input device 276 on the delivery device 12, to control the motor 44 (through the motor control circuit 272). As a further alternative or addition, the processor 271 may respond to inputs received by receiver electronics 278 from, for example, a CCD 16 or computer 18 (FIG. 1) to control the motor 44 (through the motor control circuit 272). The processor 270 may be connected to a sensor or monitor 14 to receive data representing a sensed condition (such as, but not limited to, a blood glucose level condition). The delivery device 12 may include a display device 280 for displaying information to the patient-user, where the processor 271 may be connected to control the display device 280. Suitable programs for controlling the processor 270 may be stored in the storage device 274 or other storage medium associated with the processor. A power source (not shown in FIG. 27), such as a battery, may be connected to various components of the electronic circuit and motor 44 shown in FIG. 27, to A partially exploded view of a delivery device 12 in accordance with a further embodiment of the invention is shown in FIG. 28, wherein a durable portion 22 of the delivery device contains electronics 270, a power source 280 for the electronics and a motor 44, as described above. The delivery device 12 in FIG. 28 also includes a disposable base portion 20 on which a reservoir canister 24 may be supported, as described above. An introducer needle 281 has a handle portion 282 and is positioned to allow the needle to be passed through the septum 27 of the reservoir 24, when the reservoir 24 is supported on the base portion 20, similar to the needle arrangement described above with respect to FIGS. 23 and 24. However, in addition to a introducer needle, the delivery device 12 in FIG. 28 also includes a second needle 284 connected to sensor electronics. For example, the second needle 284 may be connected to electronics that produce an electronic signal representative of a sensed biological state, such as, but not limited to, blood glucose level. In this manner, the delivery device 12 may include an on-board sensor (such as an on-board continuous blood glucose sensor that provides continuous sensor data). In further embodiments, other types of sensor electronics may be included in the delivery device to provide sensing data. Such sensors may comprise, but are not limited to, infrared or other forms of spectral analysis sensors (wherein the base portion 20 may be provided with an opening or window through which infrared or other radiated beams may pass to access the patient's skin below the base portion.

The electronic signal may be provided to the electronics 270, through an electrical coupling 286. The electronics 270 may include suitable electronics for processing the sensor signal. As described above, the needles 281 and 284 may be hollow needles that perform the fluid communication function, once inserted into the patient-user. Alternatively, the needles 281 and 284 may be introducer needles that introduce a cannula for providing the fluid communication function, after which the needles may be removed, leaving the cannula in place. FIGS. 29 and 30 provide additional views of an embodiment similar to that of FIG. 28.

While embodiments described above have been illustrated in the drawings with needles configured in common straight, linear configurations, the above embodiments may be employed with needle configurations designed to reduce physical stress on the patient. For example, once a delivery device has been secured to a patient-user, a needle (or canulla) is extended into the user's skin, as describe above. With the delivery device adhered to the surface of the skin, it is possible that the delivery device will move slightly relative to the needle point site, as the patient-user moves and as the patient-user's skin moves and flexes. The movement of the delivery device while the needle is extended into the patient-user's skin can apply a physical strain on the needle and, thereby cause the needle tip to move within the patient, resulting in physical discomfort to the patient.

To minimize such discomfort, a needle configuration may be employed, wherein the needle is configured to minimize the transfer of movement to the needle tip. For example, by forming a needle with multiple angles (such as multiple perpendicular angles) along its length, the transfer of motion occurring on one end of the needle to the other end of the needle can be reduced. Example needle configurations with such multiple angles are shown in FIGS. 30, 31 and 32, respectively. The needle 300 in FIG. 30 has two right-angle bends. The bends in combination with the flexible nature of the needle material result in dampening movements of the reservoir end of the needle 300 with respect to the sharp end (patient-user end) of the needle. Similarly, the needle 302 in FIG. 31 includes four right-angle bends. The needle 303 in FIG. 32 includes two right angle bends. Other configurations with angled bends, loops, spirals or the like may be employed to help dampen the transfer of motion from one end of the needle to the other. Further example of needle shapes are shown in FIGS. 33-36.

While embodiments described above employ a electrically operated pump 44 connected to a reservoir canister 24, other embodiments may employ other manners of storing infusion media and selectively dispensing the infusion media to the patient, including, but not limited to flexible bellows reservoirs, bladders, syringes or peristaltic pump devices.

Thus according to embodiments described above, an at-site delivery system could be fully disposable utilizing either a user filled reservoir or a pre-filled cartridge to deliver insulin. Alternatively, the at-site delivery system could be made of two parts, disposable portion and non-disposable portion. The disposable portion could contain all materials that are in direct contact with the medication such as reservoir body, reservoir piston, septum systems and injection needle. The non-disposable portion could contain significantly the materials that are not in contact with the medication including the drive system, pressure or force sensing system, battery, electronics, display, and non-disposable housing. The pump could be designed such that the disposable portion (user filled or pre-filled cartridge) is inserted into the non-disposable portion. In this manner, the adhesive to attach the pump would be placed on the non-disposable pump portion. Alternatively, the disposable portion could contain the bottom plate and mounting adhesive.

While particular embodiments of the present invention have been shown and described, it will be obvious to those skilled in the art that the invention is not limited to the particular embodiments shown and described and that changes and modifications may be made without departing from the spirit and scope of the claimed invention.

What is claimed is:

1. A delivery device for delivering an infusion media to a user, the device comprising:
a disposable housing portion having a base and adapted to be secured to a user;
a durable housing portion configured to be selectively engaged with and disengaged from the disposable housing portion to allow disposal of the disposable housing portion without disposing of the durable housing portion;

a reservoir for containing infusion media;
a moveable platform on the disposable housing portion and supported for movement relative to the disposable housing portion along a path of motion toward the base of the disposable housing portion, the moveable platform supporting the reservoir for movement with the moveable platform and along the same path of motion of the moveable platform toward the base of the disposable housing portion;
electrical control circuitry contained in the durable housing portion, wherein the electrical control circuitry controls the delivery of infusion media from the reservoir to the user.

2. A delivery device according to claim 1, wherein the moveable platform is a physically separate structure that is supported by but not formed unitary with the disposable housing portion.

3. A delivery device according to claim 1, wherein the moveable platform is located between the reservoir and the disposable housing portion.

4. A delivery device according to claim 1, further comprising a hollow needle supported relative to the platform to extend at least partially into the reservoir when the reservoir is supported on the platform.

5. A delivery device according to claim 4, wherein the hollow needle is attached to the platform in a position to extend at least partially into a reservoir when the reservoir is supported on the platform.

6. A delivery device according to claim 1, wherein the disposable housing portion has a top surface on which the movable platform is supported.

7. A delivery device according to claim 6, wherein the moveable platform has a top surface on which the reservoir is supported.

8. A delivery device according to claim 1, wherein the reservoir has a septum end for receiving an end of a hollow needle.

9. A delivery device according to claim 8, wherein the septum end moves relative to the disposable housing portion in conjunction with movement of the reservoir relative to the disposable housing portion.

10. A delivery device according to claim 1, where the moveable platform supports the reservoir for movement between first and second positions, the delivery device further comprising a hollow needle arranged in fluid flow communication with the reservoir when the reservoir is supported on the platform, the hollow needle having a tip adapted to pierce the skin of a user when the platform is moved into the second position.

11. A delivery device according to claim 10, wherein the disposable housing portion has a base provided with an opening, and the sharp tip of the hollow needle is arranged to extend through the opening in the base in response to the platform being moved into the second position.

12. A delivery device for delivering an infusion media to a user, the device comprising:
a housing having a base portion adapted to be secured to a user;
a reservoir for containing infusion media, the reservoir supported by the housing;
a drive device and electrical control circuitry contained in the housing for providing a controlled delivery of infusion media from the reservoir to the user;
a platform contained in the housing for receiving and supporting the reservoir;
a plurality of struts for moveably supporting the platform and selectively locking the platform in a fixed position relative to the base of the housing, wherein the platform is moveably supported by the struts when the platform is in a first position relative to the struts and wherein the platform is locked in a fixed location relative to the base of the housing when the platform is moved into a second position relative to the struts.

13. A delivery device according to claim 12, wherein each of the struts include a projection that engages the platform in a snap-fit arrangement when the platform is moved into the second position, and wherein the projections are disengaged from the platform when the platform is in the first position.

14. A delivery device according to claim 12, wherein, when the platform is in the first position relative to the struts, the platform is moveable toward the base of the housing to the second position relative to the struts and wherein the struts include a projection that engages the platform in a snap-fit arrangement, when the platform is moved into the second position relative to the struts.

15. A delivery device according to claim 12, further comprising a spring arranged to urge the platform in the direction toward the first position of the platform relative to the struts.

16. A delivery device according to claim 15, wherein the spring is located between the platform and the base of the housing to urge the platform in a direction away from the base of the housing.

17. A delivery device according to claim 12, further comprising a hollow needle supported relative to the platform to extend at least partially into the reservoir when the reservoir is supported on the platform.

18. A delivery device according to claim 17, wherein the hollow needle is attached to the platform in a position to extend at least partially into a reservoir when the reservoir is supported on the platform.

19. A delivery device for delivering an infusion media to a user, the device comprising:
a disposable housing portion adapted to be secured to a user;
a durable housing portion configured to be selectively engaged with and disengaged from the disposable housing portion to allow disposal of the disposable housing portion without disposing of the durable housing portion;
a reservoir for containing infusion media;
a moveable platform on the disposable housing portion supporting the reservoir for movement relative to the disposable housing portion;
electrical control circuitry contained in the durable housing portion, wherein the electrical control circuitry controls the delivery of infusion media from the reservoir to the user; and
a plurality of struts for moveably supporting the platform and selectively locking the platform in a fixed position relative to the disposable housing portion, wherein the platform is moveably supported by the struts when the platform is in a first position relative to the struts and wherein the platform is locked in a fixed location relative to the disposable housing portion when the platform is moved into a second position relative to the struts.

20. A delivery device according to claim 19, wherein, when the platform is in the first position relative to the struts, the platform is moveable toward the disposable housing portion to the second position relative to the struts and wherein the struts include a projection that engages the platform in a snap-fit arrangement, when the platform is moved into the second position relative to the struts.

21. A delivery device according to claim 19, wherein each of the struts include a projection that engages the platform in a snap-fit arrangement when the platform is moved into the second position, and wherein the projections are disengaged from the platform when the platform is in the first position.

22. A delivery device according to claim 21, wherein the platform has an upper surface for engaging the strut projections when the platform is in the second position.

23. A delivery device according to claim 19, further comprising a spring arranged to urge the platform in the direction toward the first position of the platform relative to the struts.

24. A delivery device according to claim 23, wherein the spring is located between the platform and the disposable housing portion to urge the platform in a direction away from the disposable housing portion.

25. A delivery device for delivering an infusion media to a user, the device comprising:
 a housing having a base portion adapted to be secured to a user;
 a reservoir for containing infusion media, the reservoir supported by the housing;
 a drive device and electrical control circuitry contained in the housing for providing a controlled delivery of infusion media from the reservoir to the user;
 a platform contained in the housing for receiving and supporting the reservoir;
 a plurality of struts for moveably supporting the platform and selectively locking the platform in a fixed position relative to the base of the housing, wherein the platform is moveably supported by the struts when the platform is in a first position relative to the struts and wherein the platform is locked in a fixed location relative to the base of the housing when the platform is moved into a second position relative to the struts; and
 a hollow needle that has a first end adapted to be extended at least partially into the reservoir when the reservoir is supported on the platform, the hollow needle having a second end having a sharp tip adapted to pierce the skin of a user when the platform is moved into a second position relative to the struts.

26. A delivery device according to claim 25, wherein the base of the housing is provided with an opening, and the sharp tip of the hollow needle is arranged to extend through the opening in the base in response to the platform being moved into the second position relative to the struts.

27. A delivery device according to claim 26, wherein the hollow needle is attached to the platform in a position to extend at least partially into a reservoir when the reservoir is supported on the platform and wherein the hollow needle moves into the second position in conjunction with the movement of the platform from the first position of the platform to the second position of the platform relative to the struts.

28. A method for delivering an infusion media to a user, the method comprising:
 providing a housing having a base portion adapted to be secured to a user;
 supporting a platform for movement on the base portion of the housing;
 supporting a reservoir for containing infusion media on the platform;
 containing a drive device and electrical control circuitry in the housing for providing a controlled delivery of infusion media from the reservoir to the user;
 wherein supporting a platform comprises providing a plurality of struts, supporting the platform on the struts for movement between first and second positions relative to the struts, and locking the platform in a fixed location relative to the base of the housing when the platform is moved into a second position relative to the struts.

29. A method according to claim 28, wherein locking the platform in a fixed location relative to the base comprises engaging the platform with a projections on the plurality of struts in a snap-fit arrangement when the platform is moved into the second position.

30. A method according to claim 28, wherein locking the platform in a fixed location relative to the base comprises moving the platform from the first position to the second position and engaging the platform with projections on the struts automatically as the platform is moved into the second position relative to the struts.

31. A method according to claim 28, further comprising arranging a first end of a hollow needle to extend at least partially into the reservoir when the reservoir is supported on the platform, arranging a second end of the hollow needle to pierce the skin of a user when the platform is moved into a second position relative to the struts.

32. A method according to claim 28, further comprising spring biasing the platform in the direction toward the first position of the platform relative to the struts.

33. A method according to claim 32, wherein spring biasing the platform comprises locating a spring between the platform and the base of the housing to urge the platform in a direction away from the base of the housing.

34. A method according to claim 28, further comprising supporting a hollow needle relative to the platform to extend at least partially into the reservoir when the reservoir is supported on the platform.

35. A method according to claim 34, wherein supporting a hollow needle comprises fixing the hollow needle to the platform in a position to extend at least partially into a reservoir when the reservoir is supported on the platform.

36. A method according to claim 28, further comprising providing an opening in the base of the housing, arranging a first end of a hollow needle to extend at least partially into the reservoir in response to the reservoir being supported on the platform, and moving the hollow needle such that a second end of the hollow needle is moved through the opening in the base in response to the platform being moved into a second position relative to the struts.

37. A method according to claim 36, wherein arranging the first end of the hollow needle comprising attaching the hollow needle to the platform in a position to extend at least partially into a reservoir when the reservoir is supported on the platform and wherein moving the hollow needle comprises moving the hollow needle into the second position in conjunction with the movement of the platform from the first position of the platform to the second position of the platform relative to the struts.

* * * * *

UNITED STATES PATENT AND TRADEMARK OFFICE
CERTIFICATE OF CORRECTION

PATENT NO.       : 7,641,649 B2                                      Page 1 of 1
APPLICATION NO.  : 11/210455
DATED            : January 5, 2010
INVENTOR(S)      : Moberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 944 days.

Signed and Sealed this

Sixteenth Day of November, 2010

David J. Kappos
*Director of the United States Patent and Trademark Office*